United States Patent [19]

Branch et al.

[11] Patent Number: 5,275,816
[45] Date of Patent: Jan. 4, 1994

[54] CEPHALOSPORIN DERIVATIVES

[75] Inventors: Clive L. Branch; Angela W. Guest; Stephen C. Finch, all of Betchworth, England

[73] Assignee: Beecham Group p.l.c, England

[21] Appl. No.: 578,662

[22] Filed: Sep. 4, 1990

[30] Foreign Application Priority Data

Sep. 4, 1989 [GB] United Kingdom ............... 8919944
May 8, 1990 [GB] United Kingdom ............... 9010264

[51] Int. Cl.$^5$ ............... C07D 501/57; A61K 31/545
[52] U.S. Cl. ................................. 424/114; 514/201;
514/206; 540/221; 540/227; 540/225
[58] Field of Search ............... 424/114; 540/227, 225, 540/221; 514/201

[56] References Cited

U.S. PATENT DOCUMENTS 4,684,639 8/1987 Burton et al. ............... 540/221
4,786,633 11/1988 Magatsuma et al. ............... 540/225
5,134,138 7/1992 Onoue et al. ............... 540/221

FOREIGN PATENT DOCUMENTS 0041768 12/1981 European Pat. Off. .
0071395 2/1983 European Pat. Off. .
0114750 8/1984 European Pat. Off. .
0115405 8/1984 European Pat. Off. .
0154132 9/1985 European Pat. Off. .
0211656 2/1987 European Pat. Off. .
0219926 4/1987 European Pat. Off. .
0308559 3/1989 European Pat. Off. .

*Primary Examiner*—Nicholas S. Rizzo
*Attorney, Agent, or Firm*—Rosenman & Colin

[57] ABSTRACT

7 α-formamido cephalosporin derivatives having a 3[N-(optionally substituted)aminothiopyridinium thiomethyl] substituent have anti-bacterial activity and are of use in anti-bacterial therapy. Processes for the preparation thereof and intermediates for use in these processes are also disclosed.

18 Claims, No Drawings

CEPHALOSPORIN DERIVATIVES

This invention relates to a class of novel β-lactam derivatives which have antibacterial activity and are of value in the treatment of infections in animals, especially mammals, including man, caused by a wide range of organisms, particularly Gram-negative organisms. The invention also relates to a process for the preparation of such compounds, intermediates for use in the preparation of the compounds and to pharmaceutical compositions comprising the antibacterially active compounds.

EP-A-0 071 395 (Beecham Group plc) discloses a class of β-lactam antibiotics having an α-formamido (formamidyl) substituent on the carbon atom adjacent to the carbonyl group of the β-lactam ring, of which a sub-group are the 7-α formamido cephalosporin derivatives of the general formula (A):

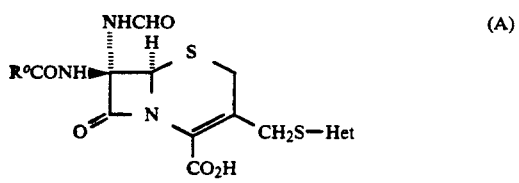

wherein $R^o$ is a group such that $R^oCONH$ is an acylamino group, in particular that found in antibacterially active cephalosporins; and 'Het' is a five or six membered heterocyclic ring containing from 1 to 4 atoms selected from N, O and S, optionally substituted with one or two groups selected from $(C_{1-6})$alkyl, $(C_{1-6})$alkoxy, hydroxyalkyl, $(C_{1-6})$alkenyl, alkoxyalkyl, carboxyalkyl, sulphonalkyl, carbamoylalkyl, trifluoromethyl, hydroxy, halogen, oxo, and (substituted)aminoalkyl, or two substituents may be linked to form the residue of a heterocyclic or a carbocyclic ring.

EP-A-0 308 559 (to Beecham Group plc) discloses a sub-group of cephalosporin derivatives of the formula (A) in which 'Het' is a tetrazolyl or triazolyl ring substituted at a ring nitrogen atom or a thiadiazolyl ring substituted at a ring carbon atom by, in each case, an amino group which may itself be optionally substituted. In the former case, amino substitution at the ring nitrogen atom does not involve the generation of a positively charged quaternary nitrogen.

In addition, EP-A-0 211 656 (to Beecham Group plc) discloses a further group of cephalosporin derivatives in which the —SHet moiety of the compounds of the formula (A) is replaced by a substituted pyridinium group, bonded via the pyridinium nitrogen, which compounds may be further described as betaines.

It has now been found that there exists another sub-group of cephalosporin derivatives, in which 'Het' is a pyridinium moiety (bonded through a ring carbon atom to sulphur) which derivatives have outstanding antibacterial properties.

Accordingly, the present invention provides a compound of formula (I) or a salt thereof:

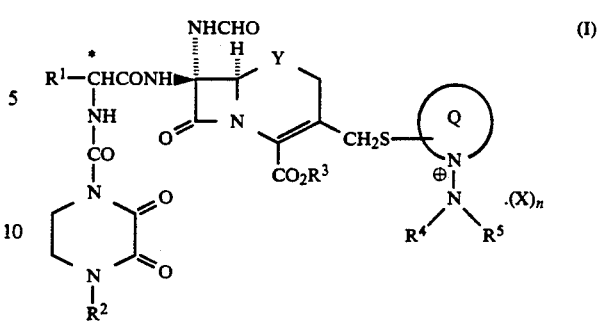

in which
Y is oxygen, sulphur, —SO—, —SO$_2$— or —CH$_2$—;
$R^1$ is phenyl, substituted phenyl, cyclohexenyl, cyclohexadienyl, 1-hydroxyethyl, 2-methylthioethyl or a 5- or 6- membered heterocyclic ring containing up to three heteroatoms selected from oxygen, sulphur or nitrogen, and optionally substituted with hydroxy, amino, halogen, $(C_{1-6})$alkylamino, di$(C_{1-6}$ alkyl)amino, or $(C_{1-6})$alkoxy;
$R^2$ is $(C_{1-8})$alkyl;
$CO_2R^3$ is carboxy or a carboxylate anion, or the group $R^3$ is a readily removable carboxy protecting group;
the moiety:

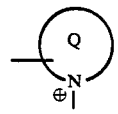

hereinafter referred to as ring Q is a pyridinium group bonded to sulphur by a ring carbon atom and which is optionally substituted at a ring carbon atom available for substitution by up to four substituents, two of which may be linked to form the residue of a heterocyclic or carbocyclic ring;

$R^4$ and $R^5$ which may be the same or different are hydrogen, optionally substituted $(C_{1-6})$alkyl, optionally substituted $(C_{3-7})$cycloalkyl, optionally substituted $(C_{5-8})$cycloalkenyl, optionally substituted $(C_{2-6})$alkenyl, optionally substituted $(C_{2-6})$alkynyl, optionally substituted $(C_{1-6})$alkylcarbonyl, optionally substituted $(C_{1-6})$alkoxycarbonyl, optionally substituted $(C_{2-6})$alkenylcarbonyl, carbamoyl, optionally substituted mono- and di-$(C_{1-6}$ alkyl)carbamoyl, optionally substituted $(C_{1-6})$alkylsulphonyl, optionally substituted hydrazinocarbonyl$(C_{1-6})$alkyl, aryl, heterocyclyl, arylcarbonyl, heterocyclylcarbonyl, mono- and di-arylcarbamoyl, N-(optionally substituted $(C_{1-6})$alkyl)N-aryl carbamoyl, arylsulphonyl, formyl, sulphonyl, N-acylcarbamoyl, or a readily removable amino protecting group; or $R^4$ and $R^5$ together with the nitrogen atom to which they are attached form an amidine or a heterocyclic group or;

$R^4$ and $R^5$ together form a $(C_{1-6})$alkylidene, $(C_{3-7})$cycloalkylidene, aryl$(C_{1-6})$alkylidene or heteroaryl$(C_{1-6})$alkylidene group and which alkylidene or cycloalkylidene moiety may be optionally substituted;

X is an inorganic or organic anion; and n is 0 or 1, with the proviso that when:

(i) $CO_2R^3$ is carboxylate, n is 0, and (ii) $CO_2R^3$ is carboxy or the group $R^3$ is a readily removable carboxy protecting group, then n is 1 and the anion X is present in the appropriate stoichiometric proportion to balance the positive charge on the pyridinium group.

It will be appreciated that the compounds of formula (I) are quaternary salts and the positive charge on the pyridinium group must always be balanced by a counter anion. The counter anion may be present on a negatively charged group within the molecule, such as the carboxylate anion $CO_2R^3$ (when n is 0), or the counter anion may be present as an external anion X (when n is 1).

In compounds of formula (I), the formamido group can exist in conformations wherein the hydrogen atoms of the —NH—CHO moiety are cis- or trans-; of these the cis conformation normally predominates.

When used herein the term 'aryl' includes phenyl and naphthyl each optionally substituted with up to five, preferably up to three groups.

When used herein the terms 'heterocyclyl' and 'heterocyclic' suitably include, unless otherwise defined, aromatic and non-aromatic, single and fused, rings suitably containing up to four heteroatoms in each ring selected from oxygen, nitrogen and sulphur, which rings may be unsubstituted or substituted by, for example, up to three groups. Each heterocyclic ring suitably has from 4 to 7, preferably 5 or 6, ring atoms. A fused heterocyclic ring system may include carbocyclic rings and need include only one heterocyclic ring.

Some examples of optional substituents in groups such as alkyl, cycloalkyl, alkenyl, cycloalkenyl, alkynyl, alkoxy, alkylidene, cycloalkylidene, ring Q, aryl, and heterocyclyl, mentioned hereinbefore as being optionally substituted include, unless otherwise defined, up to three groups (which may be the same or different) chosen from:

(i) halogen, cyano, azido, nitro, phthalimido, formyl, carboxy, carboxylate salts, sulphonyl, sulphonate salts, or oxo;

(ii) amino, hydrazino, guanidino, carbamoyl, or sulphonamido, in each of which groups a nitrogen may be further optionally substituted by one or two groups (which may be the same or different) selected from the groups listed in subparagraphs (iv), (v) and (vi);

(iii) hydroxy, oxyimino, or mercapto, in each of which groups hydrogen may be replaced by one of the groups listed in subparagraphs (iv), (v) and (vi);

(iv) a group $R^p$ wherein $R^p$ denotes aryl, or heterocyclyl;

(v) a group $R^q$ wherein $R^q$ denotes $C_{1-6}$ alkyl, $C_{3-7}$cycloalkyl, $C_{2-6}$alkenyl, $C_{5-8}$cycloalkenyl, or $C_{2-6}$alkynyl, each of which groups $R^q$ may be further optionally substituted by up to three groups (which may be the same or different) chosen from the groups listed in subparagraphs (i), (ii), (iii), (iv) and (vi); and (vi) a group $R^pCO$—, $R^pOCO$—, $R^qCO$—, $R^qO$-CO—, $R^pSO$—, $R^pSO_2$—, $R^qSO$—, or $R^qSO_2$— wherein $R^p$ and $R^q$ are as defined in subparagraphs (iv) and (v) respectively.

When used herein, the term 'halogen' refers to fluorine, chlorine, bromine and iodine.

Preferably a substituent for an alkyl, cycloalkyl, alkenyl, cycloalkenyl, alkylidene, cycloalkylidene, or alkynyl group is selected from halogen, cyano, azido, nitro, carboxy, $(C_{1-6})$alkoxycarbonyl, carbamoyl, mono- or di-$(C_{1-6})$alkylcarbamoyl, sulphono, sulphamoyl, mono- and di-$(C_{1-6})$alkylsulphamoyl, amino, mono- and di-$(C_{1-6})$alkylamino, acylamino, $(C_{1-6})$alkoxycarbonylamino, aryl, heterocyclyl, hydroxy, $(C_{1-6})$alkoxy, acyloxy, oxo, arylcarbonyl, heterocyclylcarbonyl, $(C_{1-6})$alkylthio, $(C_{1-6})$alkanesulphinyl, and $(C_{1-6})$alkanesulphonyl.

Preferably a substituent for an aryl group is selected from halogen, $(C_{1-6})$alkyl, phenyl, $(C_{1-6})$alkoxy, hydroxy$(C_{1-6})$alkyl, mercapto$(C_{1-6})$alkyl, halo$(C_{1-6})$alkyl, mercapto, hydroxy, amino, mono- or di-$(C_{1-6})$alkylamino, nitro, carboxy, $(C_{1-6})$alkoxycarbonyl, $(C_{1-6})$alkoxycarbonyl$(C_{1-6})$alkyl, $(C_{1-6})$alkylcarbonyloxy, formyl, or $(C_{1-6})$alkylcarbonyl.

Preferably a substituent for a heterocyclyl group or a substituent for the ring Q is selected from halogen, $(C_{1-6})$alkyl, $(C_{1-6})$alkoxy, $(C_{1-6})$alkoxy$(C_{1-6})$alkyl, halo$(C_{1-6})$alkyl, hydroxy, amino, mono- and di-$(C_{1-6})$alkylamino, acylamino, carboxy, carboxy salts, carboxy esters, carbamoyl, $(C_{1-6})$alkoxycarbonyl, aryloxycarbonyl, $(C_{1-6})$alkoxycarbonyl$(C_{1-6})$alkyl, aryl, and oxo groups.

The carbon atom marked * in formulae herein is asymmetric and thus compounds of formula (I) may exist as two optically active diastereoisomers. In general the isomer prepared from the D-side chain exhibits the highest antibacterial activity and accordingly the D compound or the DL mixtures are preferred, with the D compound being particularly preferred.

The compounds of formula (I) with the preferred D-side-chain can be separated from a mixture of both diastereoisomers by conventional methods, or prepared from intermediates that bear a D- side chain.

Suitably the substituted phenyl group for $R^1$ is a phenyl group substituted with up to three groups selected from $(C_{1-6})$alkyl, phenyl, halogen, amino, nitro, hydroxy, $(C_{1-6})$alkylamido, carbamoyl, carboxy, $(C_{1-6})$alkoxycarbonyl, aryloxycarbonyl, halo $(C_{1-6})$ alkyl, hydroxy$(C_{1-6})$alkyl, oxo$(C_{1-6})$alkyl, $(C_{1-6})$alkylcarbonyl, arylcarbonyl, $(C_{1-6})$alkylamino, di$(C_{1-6})$alkylamino, or sulphonamido, any amino and hydroxy groups being optionally protected.

The optional protecting groups for hydroxy or amino groups attached to the phenyl ring in $R^1$ are suitably readily cleaved and include in vivo hydrolysable groups as well as groups which may be cleaved by conventional chemical or enzymatic methods.

A comprehensive discussion of the ways in which hydroxy and amino groups may be protected and methods for cleaving the resulting protected derivatives is given in, for example, 'Protective Groups in Organic Synthesis' by T. W. Greene (Wiley-Interscience, New York, 1981). Particularly suitable protecting groups include those which, when protecting a hydroxy group in $R^1$, afford esters or carbonates (both of which may be in vivo hydrolysable), ethers (including silyl ethers) and acetals (for example tetrahydropyranyloxy derivatives, sometimes described as 'THP ethers'). When $R^1$ is aminophenyl, suitable protecting groups include, for example, amides and carbamates.

When $R^1$ is dihydroxyphenyl, for example 3,4-dihydroxyphenyl, it will be understood that one or both of the hydroxy groups may be protected. When both hydroxy groups are protected it will be understood that a different protecting group may be used for each hydroxy group, although, more conveniently, the protecting groups used will be the same.

Examples of suitable protecting groups for a hydroxy group in $R^1$ include formyl and optionally substituted $(C_{1-6})$alkylcarbonyl and arylcarbonyl groups such as acetyl, chloroacetyl, dichloroacetyl and benzoyl; optionally substituted ($C_{1-6}$)alkoxycarbonyl and aryl ($C_{1-6}$)alkoxycarbonyl, for example ethoxycarbonyl, trimethylsilylethoxycarbonyl, benzyloxycarbonyl and 4-nitrobenzyloxycarbonyl; and optionally substituted ($C_{2-6}$)alkenyloxycarbonyl such as allyloxycarbonyl.

Further examples of suitable protecting groups for a hydroxy group in $R^1$ include aryl($C_{1-6}$)alkyl and silyl groups.

Preferred aryl($C_{1-6}$)alkyl protecting groups include benzyl, 4-methoxybenzyl and 4-nitrobenzyl.

Preferred silyl protecting groups may be substituted with ($C_{1-6}$)alkyl and/or phenyl groups and include, for example, trimethylsilyl, t-butyldimethylsilyl, t-butyldiphenylsilyl, triethylsilyl, isopropyldimethylsilyl, triphenylmethyldimethylsilyl and the like. The resulting silyl ethers may be cleaved by methods known in the art, such as those described by T. W. Greene (loc. cit.) or by M. Lalonde and T. H. Chan in *Synthesis*, 1985 (September), pages 817-845 and references therein.

It will be understood that hydroxy groups mentioned herein as 'protected' may suitably be protected by groups mentioned hereinabove as suitable for protecting hydroxy groups present in $R^1$.

Particularly preferred hydroxy protecting groups are acetyl, 4-methoxybenzyl and trimethylsilyl.

Suitable groups for $R^1$ include phenyl, 3,4-dihydroxyphenyl, 3,4-diacetoxyphenyl, 4-hydroxyphenyl, 4-acetoxyphenyl, 4-aminophenyl, 2-thienyl and 1-hydroxyethyl.

Suitable values for the group $R^2$ include ($C_{1-6}$)alkyl, for example methyl, ethyl, propyl and butyl.

A preferred value for the group $R^2$ is ethyl.

Suitable values for the groups $R^4$ and $R^5$ include, for example, ($C_{1-6}$)alkyl, ($C_{1-6}$)alkenyl, each of which may be optionally substituted, hydrogen, aryl, optionally substituted ($C_{0-6}$)alkylcarbonyl, arylcarbonyl and heterocyclylcarbonyl, or the groups $R^4$ and $R^5$ may together with the nitrogen atom to which they are attached form a heterocyclic group.

Specific examples of the groups $R^4$ and $R^5$ include hydrogen, methyl, prop-2-en-1-yl, benzyl, phenyl, carbamoylmethyl, carboxymethyl, 2-hydroxyethyl, t-butoxycarbonylmethyl, formyl, acetyl, 3,4-dihydroxybenzoyl, p-nitrobenzoyl, p-methoxybenzoyl, 3,4-dihydroxycinnamoyl, and 2-furoyl.

Suitable values for the groups $R^4$ and $R^5$, when acting as readily removable protecting groups, include amides and carbamates, for instance t-butoxycarbonyl.

When the groups $R^4$ and $R^5$ and the nitrogen atom to which they are attached form a heterocyclic group, specific examples thereof include pyrrolidinyl, morpholinyl, piperazinyl, and hexahydroazepinyl.

Preferably the group $R^5$ is hydrogen or ($C_{1-6}$)alkyl.

Included within the scope of readily removable carboxy protecting groups for $R^3$ are, for example, ester groups including pharmaceutically acceptable in vivo hydrolysable ester groups.

Suitable substituents for the pyridinium group of the ring Q include a ($C_{1-6}$) alkylene, for instance, a —($CH_2$)$_3$—, group, forming the residue of a carbocyclic ring.

It will be appreciated that also included within the scope of the invention are salts and carboxy-protected derivatives, including in vivo hydrolysable esters, of any carboxy groups that may be present as optional substitutents in compounds of formula (I). Also included within the scope of the invention are acid addition salts of any amino or substituted amino groups that may be present as optional substituents in compounds of formula (I).

It will be appreciated that in the ring Q, the pyridinium group may be bonded to sulphur by a carbon which is $\alpha$-, $\beta$- or $\gamma$-, preferably $\alpha$- or $\gamma$-, more preferably $\gamma$-, to the pyridinium nitrogen.

Since the $\beta$-lactam antibiotic compounds of the present invention are intended for use in pharmaceutical compositions, it will be readily appreciated that preferred compounds within formula (I) are pharmaceutically acceptable, i.e. are compounds of formula (Ia) or pharmaceutically acceptable salts or pharmaceutically acceptable in vivo hydrolysable esters thereof:

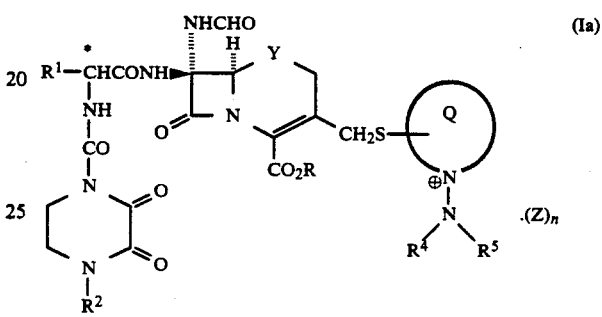

in which $R^1$, $R^2$, $R^4$, $R^5$, ring Q, Y, n, and * are as defined with respect to formula (I) with the proviso that neither $R^4$ and $R^5$ is a readily removable amino protecting group, the group $CO_2R$ is carboxy or a carboxylate anion and Z is a pharmaceutically acceptable inorganic or organic anion present in the appropriate stoichiometric proportion to balance the positive charge on the ring Q.

Suitable values of Z include chloride, bromide, iodide, phosphate (i.e. $\frac{1}{3}$ $PO_4^{3-}$), and sulphate (i.e. $\frac{1}{2}$ $SO_4^{2-}$), when the anion is an inorganic anion; and acetate, hydrogen maleate, hydrogen fumarate, dihydrogen citrate, and methyl sulphonate, when the anion is an organic anion.

Non-pharmaceutically acceptable salts of the compound of formula (I) wherein $R^3$ is hydrogen are primarily of use as intermediates in the preparation of a compound of formula (Ia) wherein $R^3$ is hydrogen or a pharmaceutically acceptable salt thereof. Salts within compounds of formula (I) may be prepared by salt exchange in conventional manner.

Similarly, carboxy protected derivatives of formula (I), i.e. those compounds of formula (I) wherein $R^3$ is a readily removable carboxy protecting group, may be used as intermediates in the preparation of a compound of the formula (Ia) wherein $R^3$ is hydrogen, or a pharmaceutically acceptable salt thereof. Included within the scope of readily removable carboxy protecting groups for $R^3$ are ester groups including pharmaceutically acceptable in vivo hydrolysable ester groups.

From the foregoing, it will be appreciated that within the compounds of the formula (Ia) there exist a subgroup of compounds of the formula (Ib):

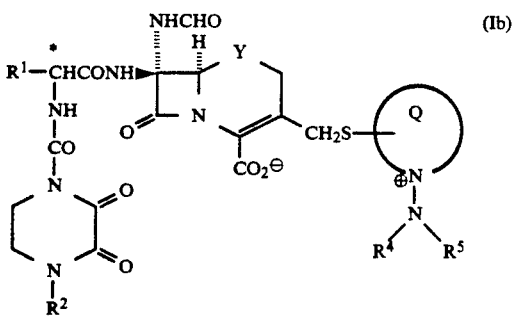

(Ib)

wherein $R^1$, $R^2$, $R^4$, $R^5$, Y, ring Q and * are defined with respect to formula (Ia);

which compounds of formula (Ib) may also be described as betaines, a betaine being defined as an uncharged species having isolated non-adjacent cationic and anionic sites, and not possessing a hydrogen atom bonded to the cationic site.

There also exists within the compounds of formula (Ia) a second sub-group, the compounds of the formula (Ic):

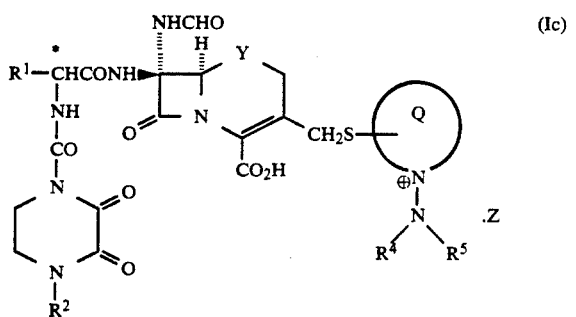

(Ic)

wherein $R^1$, $R^2$, $R^4$, $R^5$, Y, Z, ring Q and * are defined with respect to formula (Ia).

Since the β-lactam antibiotic compounds of the present invention are intended for use in pharmaceutical compositions, it will be further understood that they are each provided in substantially pure form, for example at least 50% pure, more suitably at least 75% pure and preferably at least 95% pure (% are on a wt/wt basis). Impure preparations of the compounds may be used for preparing the more pure forms used in the pharmaceutical compositions. Although the purity of intermediate compounds of the present invention is less critical, it will be readily understood that the substantially pure form is preferred for the β-lactam antibiotic compounds. Preferably, whenever possible, the compounds of the present invention are obtained in crystalline form.

When some of the compounds of this invention are allowed to crystallise, or are recrystallised, from organic solvents, solvent of crystallisation may be present in the crystalline product. This invention includes within its scope such solvates. Similarly, some of the compounds of this invention may be crystallised or recrystallised from solvents containing water. In such cases water of hydration may be formed. This invention includes within its scope stoichiometric hydrates as well as compounds containing variable amounts of water that may be produced by processes such as lyophilisation.

Suitable readily removable carboxyl protecting groups for the group —$CO_2R^3$ include groups forming ester derivatives of the carboxylic acid, including in vivo hydrolysable esters. The derivative is preferably one which may readily be cleaved.

Suitable ester-forming carboxyl-protecting groups are those which may be removed under conventional conditions. Such groups for $R^3$ include benzyl, p-methoxybenzyl, benzoylmethyl, p-nitrobenzyl, 4-pyridylmethyl, 2,2,2-trichloroethyl, 2,2,2-tribromoethyl, t-butyl, t-amyl, allyl, diphenylmethyl, triphenylmethyl, adamantyl, 2-benzyloxyphenyl, 4-methylthiophenyl, tetrahydrofuran-2-yl, tetrahydropyran-2-yl, pentachlorophenyl, acetonyl, p-toluenesulphonylethyl, methoxymethyl, a silyl, stannyl or phosphorus-containing group, an oxime radical of formula —N=$CHR^6$ where $R^6$ is aryl or heterocyclic, or an in vivo hydrolysable ester radical such as defined below.

A carboxyl group may be regenerated from any of the above esters by usual methods appropriate to the particular $R^3$ group, for example, acid- and base-catalysed hydrolysis, or by enzymically-catalysed hydrolysis, or by hydrogenolysis under conditions wherein the remainder of the molecule is substantially unaffected.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

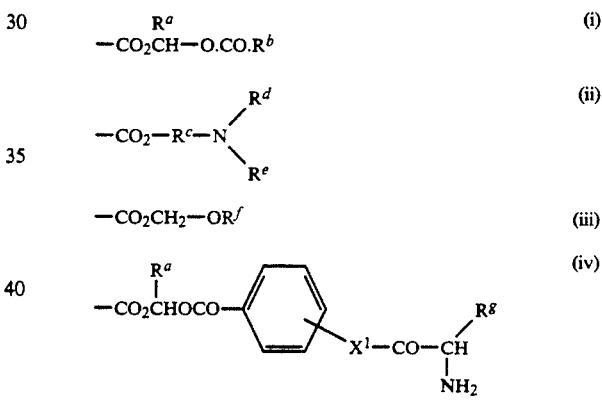

wherein $R^a$ is hydrogen, $(C_{1-6})$alkyl, $(C_{3-7})$cycloalkyl, methyl, or phenyl; $R^b$ is $C_{1-6}$)alkyl, $(C_{1-6})$alkoxy, phenyl, benzyl, $(C_{3-7})$cycloalkyl, $(C_{1-6})$alkyl$(C_{3-7})$cycloalkyl, 1-amino$(C_{1-6})$alkyl, or 1-$(C_{1-6}$alkyl)amino$(C_{1-6})$alkyl; or $R^a$ and $R^b$ together form a 1,2-phenylene group optionally substituted by one or two methoxy groups; $R^c$ is $(C_{1-6})$alkylene optionally substituted with a methyl or ethyl group and $R^d$ and $R^e$ independently are $(C_{1-6})$alkyl; $R^f$ is $(C_{1-6})$alkyl; $R^g$ is hydrogen or phenyl optionally substituted by up to three groups selected from halogen, $(C_{1-6})$alkyl, or $(C_{1-6})$alkoxy; and $X^1$ is oxygen or NH.

Examples of suitable pharmaceutically acceptable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

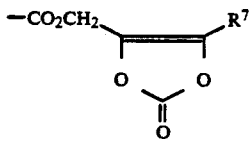

wherein $R^7$ is hydrogen, $(C_{1-6})$alkyl or phenyl.

Suitable pharmaceutically acceptable salts of the carboxy group of the compound of formula (I) include metal salts, for example aluminium, alkali metal salts such as sodium or potassium, alkaline earth metal salts such as calcium or magnesium; and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-methylmorpholine, N-ethylpiperidine, N-benzyl-β- phenethylamine, o dehydroabietylamine, N,N'-bisdehydro-abietylamine, ethylenediamine or N-methylglucosamine; or basic amino acids such as lysine, arginine, or bases of the pyridine type such as pyridine, collidine or quinoline; or other amines which have been used to form salts with known penicillins and cephalosporins. Other useful salts include the lithium salt and silver salt.

One particularly preferred sub-group of compounds within the present invention are compounds of formula (II):

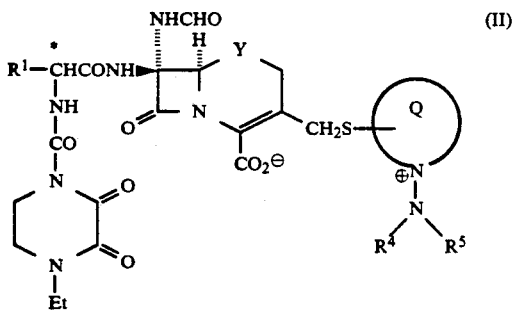

wherein $R^1$ is phenyl or substituted phenyl as hereinbefore defined, and Y, $R^4$, $R^5$, ring Q, and * are as defined with respect to formula (I).

Specific classes of compounds within compounds of formulae (I), (Ia), (Ib), (Ic) and (II) as hereinbefore defined are those compounds in which Y is sulphur.

Specific compounds within this invention include the following and pharmaceutically acceptable salts and in-vivo hydrolysable esters thereof:

[6R,7R]-3-[1-(3,4-Dihydroxybenzoylamino)pyridinium-4-thiomethyl]-7-[[R]-2-[(4-ethyl-2,3-dioxopiperazin-1-yl) carbonylamino]-2-phenylacetamido]-7-formamidoceph-3-em-4-carboxylate;

[6R,7R]-3-[1-(Dimethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate;

[6R,7R]-3-[1-(N-Benzyl-N-methylamino)pyridinium-4-thiomethyl]-7-[[R]-2-[(4-ethyl-2,3-dioxopiperazin-1-yl) carbonylamino]-2-phenylacetamido]-7-formamidoceph-3-em-4-carboxylate;

[6R,7R]-3-[1-(N-Carbamoylmethyl-N-methylamino)-pyridinium-4-thiomethyl]-7-[[R]-2-[(4-ethyl-2,3-dioxopiperazin-1-yl)carbonylamino]-2-phenyl acetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-(3,4-dihydroxybenzoyl)-N-methylamino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-(3,4-dihydroxycinnamoyl)-N-methylamino]-pyridinium-4-thiomethyl]ceph-3-em-4-carboxylate;

6R,7R]-7-[[R]-2-[(4-Ethyl-2,3-dioxopiperazin-1-yl) carbonylamino]-2-phenylacetamido]-7-formamido-3-[1-methylamino)pyridinium-4-thiomethyl]ceph-3-em-4-carboxylate;

[6R, 7R]-7-[[R]-2-[(4-Ethyl-2,3-dioxopiperazin-1-yl)carbonylamino]-2-phenylacetamido]-7-formamido-3-[1-(N- acetyl-N-methylamino)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(N-formyl-N-methylamino)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(4-nitrobenzoyl)amino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(4-methoxybenzoyl)amino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(2-furoyl)amino]pyridinium-4-thiomethyl]ceph-3-em-4-carboxylate;

[6R,7R]-3-(1-Aminopyridinium-4-thiomethyl)-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(Carboxymethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(Diphenylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-[N-(2-hydroxyethyl)-N-methylamino]pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-(hexahydro-1H-azepin-1-yl)pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-[4-(2-hydroxyethyl)piperazin-1-yl]pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-(morpholin-4-yl)pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(2-oxopyrrolidin-1-yl)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(2-oxopiperidin-1-yl)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[(prop-2-en-1-yl)amino]pyridinium-4-thiomethyl]-ceph-3-em-4-carboxylate;

[6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate;

[6R,7R]-3-(1-Aminopyridinium-4-thiomethyl)-7-[[R]-2-(3,4-dihydroxyphenyl)-2-[(4-ethyl-2,3-dioxopiperazin-yl)carbonylamino]acetamido]-7-formamidoceph-3-em-4-carboxylate;

[6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate;

[6R,7R]-3-[1-(Carboxymethylamino)pyridinium-4-thiomethyl]-7-[[R]-2-(3,4-dihydroxyphenyl)-2-[(4-ethyl-2,3-dioxopiperazin-1-yl)carbonylamino]acetamido]-7-formamidoceph-3-em-4-carboxylate; and

[6R,7R]-3-(1-Amino-2,3-cyclopentenopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate.

The antibiotic compounds according to the invention may be formulated for administration in any convenient way for use in human or veterinary medicine, according to techniques and procedures per se known in the art with reference to other antibiotics, and the invention therefore includes within its scope a pharmaceutical composition comprising an antibiotic compound according to the present invention such as, for example a pharmaceutically acceptable compound of formula (I) or a salt or in vivo hydrolysable ester thereof together with a pharmaceutically acceptable carrier or excipient. The compositions may be formulated for administration by any suitable route, such as oral or parenteral, or by topical application. Normally, administration will be via a parenteral route. The compositions may be in the form of tablets, capsules, powders, granules, lozenges, creams or liquid preparations, such as oral or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinylpyrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, methyl cellulose, glucose syrup, gelatin, hydroxyethylcellulose, carboxymethyl cellulose, aluminium stearate gel or hydrogenated edible fats; emulsifying agents, for example lecithin, sorbitan monooleate, or acacia; non-aqueous vehicles (which may include edible oils), for example almond oil, oily esters, glycerine, propylene glycol, or ethyl alcohol; preservatives, for example methyl or propyl p-hydroxybenzoate or sorbic acid; and, if desired, conventional flavouring or colouring agents. Suppositories will contain conventional suppository base, e.g. cocoa-butter or other glyceride.

For parenteral administration, fluid unit dosage forms are prepared utilising the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as local anaesthetic, preservative and buffering agents can be dissolved in the vehicle. To enhance the stability, the composition can be frozen after filling into the vial and the water removed under vacuum. The dry lyophilised powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilisation cannot be accomplished by filtration. The compound can be sterilised by exposure to ethylene oxide before suspending in the sterile vehicle. Advantageously, a surfactant or wetting agent is included in the composition to facilitate uniform distribution of the compound.

The composition may contain from 0.1% to 99.5% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 mg to 12 g per day for an average adult patient (body weight 70 kg), for instance 1500 mg per day, depending on the route and frequency of administration. Such dosages correspond to approximately 1.5 to 170 mg/kg per day. Suitably the dosage is from 1 to 6 g per day.

The daily dosage is suitably given by administering a compound of the invention several times in a 24-hour period. Typically, 250 mg is administered 4 times a day although, in practice, the dosage and frequency of administration which will be most suitable for an individual patient will vary with the age, weight and response of the patients, and there will be occasions when the physician will choose a higher or lower dosage and a different frequency of administration. Such dosage regimens are within the scope of this invention.

No toxicological effects are indicated when a pharmaceutically acceptable compound of the invention of formula (I) or a salt or in vivo hydrolysable ester thereof is administered in the above mentioned dosage range.

The antibiotic compounds according to the present invention may be the sole therapeutic agent in the compositions of the invention or a combination with other antibiotics and/or β-lactamase inhibitors may be employed.

Advantageously the compositions also comprise a compound of formula (III) or a pharmaceutically acceptable salt or ester thereof:

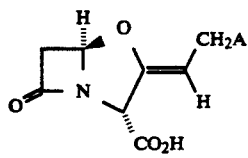

wherein A is hydroxyl; substituted hydroxyl; thiol; a group of formula $SO_2R^8$ wherein $R^8$ is $(C_{1-6})$alkyl; substituted thiol; amino; mono- or di-(hydrocarbyl) substituted amino; mono- or di-acylamino; an optionally substituted triazolyl group; or an optionally substituted tetrazolyl group as described in EP-A-0 053 893 (to Beecham Group plc).

A further advantageous composition comprises a pharmaceutically acceptable antibiotic compound of the formula (I) or a salt or in vivo hydrolysable ester thereof and a pharmaceutically acceptable carrier or excipient together with a β-lactamase inhibitor of formula (IV) or a pharmaceutically acceptable salt or in vivo hydrolysable ester thereof:

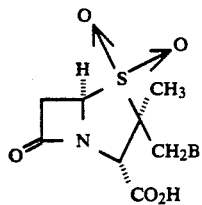

wherein B is hydrogen, halogen or a group of formula:

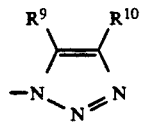

in which $R^9$ and $R^{10}$ are the same or different and each is hydrogen, $(C_{1-6})$alkoxycarbonyl, or carboxy or a pharmaceutically acceptable salt thereof.

Further suitable β-lactamase inhibitors include 6-alkylidene penems as described in EP-A-0 041 768 and EP-A-0 154 132 (to Beecham Group plc).

Further suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of a pharmaceutically acceptable antibiotic compound of the present invention of the formula (I) or a salt or in vivo hydrolysable ester thereof.

In a further aspect, the present invention also provides for the use of a pharmaceutically acceptable compound of the formula (I) or a salt or an in vivo hydrolysable ester thereof for the manufacture of a medicament.

The pharmaceutically acceptable antibiotic compounds of the present invention of formula (I) or salts or in vivo hydrolysable esters thereof are active against a broad range of Gram-positive and Gram-negative bacteria, and may be used to treat a wide range of bacterial infections including those in immunocompromised patients.

Amongst many other uses, the pharmaceutically acceptable compounds of the invention of formula (I) or salts or in vivo hydrolysable esters thereof are of value in the treatment of respiratory tract and urinary tract infections in humans and may also be used to treat mastitis in cattle. A particular advantage of the antibacterially active compound of this invention is their stability to β-lactamase enzymes and they are therefore effective against β-lactamase producing organisms.

The present invention further provides a process for the preparation of a compound of formula (I) which process comprises treating a compound of formula (V):

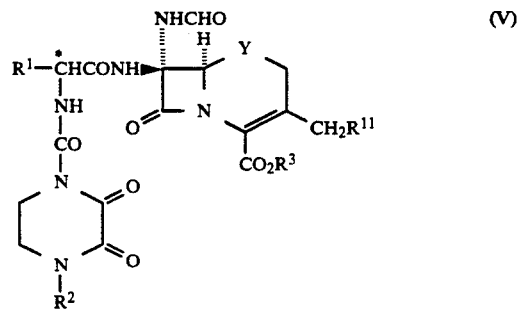

wherein $R^1$, $R^2$, $R^3$, Y and * are as hereinbefore defined, and $R^{11}$ is a leaving group; and wherein any reactive groups may be protected;

with a thiopyridone compound of formula (VI):

wherein $R^4$ and $R^5$ are as hereinbefore defined, and the moiety:

is such that it is converted to ring Q (as hereinbefore defined) in situ during the course of the reaction;

with the proviso that when $R^{11}$ is an acyloxy group —$CO_2R^3$ must be in the free acid form or a salt thereof;

and thereafter if necessary carrying out one or more of the following steps:

i) converting each or any one of the groups $R^3$, $R^4$ and $R^5$ into a different group $R^3$, $R^4$ and $R^5$;

ii) removing any protecting groups; or iii) converting the product into a salt.

At the end of the process described hereinabove and in other processes for the preparation of the compound of formula (I) described hereinbelow it may be necessary to remove protecting groups. Deprotection may be carried out by any convenient method known in the art that does not cause unwanted side reactions to occur to any appreciable extent. Methods that are particularly suitable for converting an acetoxy group in $R^1$ into a hydroxy group include treatment with aqueous sodium sulphite solution or aqueous sodium hydrogen carbonate solution, or treatment with an esterase, especially citrus acetylesterase. When a hydroxy group in $R^1$ is protected as a silyl ether, for example the trimethylsilyl ether, removal of the silyl group is normally carried out by acid hydrolysis.

Suitable leaving groups $R^{11}$ include halo such as chloro, bromo or iodo or an acyloxy group such as, for example, the acetoxy group. Preferred groups for $R^{11}$ are chloro, bromo and iodo.

This reaction is desirably conducted in a solvent. For example, use can be made of water or of an organic solvent which is inert to the starting compounds, such as dimethylformamide, dimethylacetamide, dioxane, acetone, dichloromethane, 1,2-dichloroethane, acetonitrile, dimethylsulfoxide or tetrahydrofuran, or mixtures thereof. The reaction temperature and time depend, among other factors, upon the starting compounds and solvent to be employed but generally the reaction is carried out at a selected temperature within the range of 0° to 100° C. for a selected time of a few minutes to several days.

Compounds of formula (V) wherein $R^{11}$ is acyloxy may be prepared by analogy with procedures described in EP-A-0 115 405 and EP-A-0 071 395 (to Beecham Group plc).

Certain compounds of formula (V) wherein $R^{11}$ is halo and salts and protected derivatives thereof are novel and valuable intermediates. Accordingly these compounds form another aspect of the present invention.

Preferred compounds of the formula (V) include salts and esters in which $R^3$ is as hereinbefore defined and in particular in which $R^3$ is diphenylmethyl, p-methoxybenzyl or trimethylsilyl.

Specific compounds within formula (V) wherein $R^{11}$ is halo include the following compounds:
Diphenylmethyl [6R,7R]-3-(chloromethyl)-7-[[R]-2-[(4-ethyl-2,3-dioxopiperazin-1-yl)carbonylamino]-2-phenyl-acetamido]-7-formamidoceph-3-em-4-carboxylate;
Diphenylmethyl [6R,7R]-3-(bromomethyl)-7-[[R]-2-[(4-ethyl-2,3-dioxopiperazin-1-yl)carbonylamino]-2phenylacetamido]-7-formamidoceph-3-em-4-carboxylate;
Diphenylmethyl [6R,7R]-[[R]-2-(3,4-Diacetoxyphenyl)-2-[(4-ethyl-2,3-dioxopiperazin-1-yl)carbonylamino]acetamido]-7-formamido-3-(halomethyl)ceph-3-em-4-carboxylate;
Diphenylmethyl [6R,7R]-7-[[R]-2-(3,4-dihydroxyphenyl)-2-[(4-ethyl-2,3-dioxopiperazin-1-yl)carbonylamino]acetamido]-7-formamido-3-(halomethyl)ceph-3-em-4-carboxylate;
and analogous derivatives in which the C-4 carboxy group is blocked by another readily removable carboxy protecting group.

Compounds of formula (VI) may be prepared by treatment of the corresponding thiopyranone with a hydrazine derivative of the formula (VII):

$$H_2NNR^4R^5 \qquad (VII)$$

wherein $R^4$ and $R^5$ are as hereinbefore defined, by analogy with the process described by Ibrahim El-Sayad El-Kholy et al., *J. Het. Chem.*, 1974, 11, 487.

Alternatively, compounds of formula (VI) may be obtained by treating the corresponding pyridone with, for instance, Lawesson's reagent or phosphorus pentasulphide, according to conventional procedures. Suitable pyridones may be prepared according to the methodology of Freeman et al, *J. Amer. Chem. Soc.*, 1947, 69, 858.

Included within the compounds of formula (VI) are sub-groups of compounds of the formulae (VIa) and (VIb).

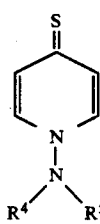

(VIa)

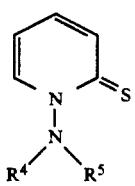

(VIb)

wherein $R^4$ and $R^5$ are as hereinbefore defined; and the 4- or 2-thiopyridone ring may be optionally substituted at a ring carbon atom available for substitution by up to four substituents, two of which may be linked to form the residue of a heterocyclic or carbocyclic ring.

It will be appreciated that within the process hereinbefore described there exists a specific process in which in the compound of formula (V), Y is sulphur, —SO— or —SO$_2$—.

The compounds of formula (I) may also suitably be prepared by reacting a compound of formula (VIII) or a salt thereof:

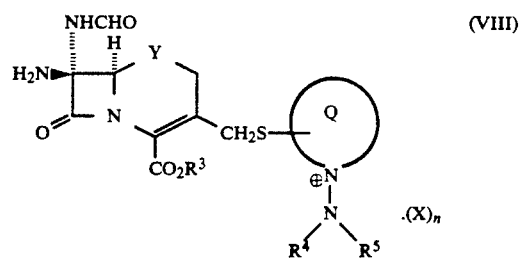

(VIII)

wherein $R^3$, $R^4$, $R^5$, X, Y, ring Q, and n are as hereinbefore defined, the 7β-amino group is optionally substituted with a group which permits acylation to take place; and any reactive groups may be protected;
with an N-acylating derivative of an acid of formula (IX):

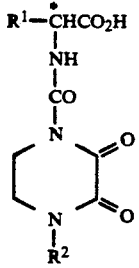

(IX)

wherein $R^1$, $R^2$, and * are as hereinbefore defined, and wherein any reactive groups may be protected; and thereafter, if necessary, carrying out one or more of the following steps:

i) converting each or any one of the groups $R^3$, $R^4$ and $R^5$ into a different group $R^3$, $R^4$ and $R^5$;
ii) removing any protecting groups; or
iii) converting the product into a salt.

Preferred compounds of the formula (VIII) include salts and esters in which $R^3$ is as hereinbefore defined and in particular in which $R^3$ is diphenylmethyl, p-methoxybenzyl or trimethylsilyl.

Suitable groups which permit acylation to take place and which are optionally present on the amino group of the starting material of the formula (VIII) include silyl, stannyl and phosphorus groups, for example trialkylsilyl groups such as trimethylsilyl, trialkyltin groups such as tri-n-butyltin, phosphorus groups of formula —$PR^{12}R^{13}$ wherein $R^{12}$ is an alkyl, haloalkyl, aryl, aralkyl, alkoxy, haloalkoxy, aryloxy, aralkyloxy or dialkylamino group, $R^{12}$ is the same as $R^{13}$ or is halogen or $R^{12}$ and $R^{13}$ together form a ring; suitable such phosphorus groups being —$P(OC_2H_5)_2$, —$P(C_2H_5)_2$,

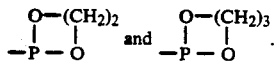

A group which may optionally be introduced in situ prior to acylation onto the amino group in the compound of formula (VIII) is trimethylsilyl.

An appropriate reactive N-acylating derivative of the acid (IX) is employed in the above process.

Suitable N-acylating derivatives include an acid halide, preferably the acid chloride or bromide. Acylation with an acid halide may be effected in the presence of an acid binding agent, for example a tertiary amine (such as pyridine or dimethylaniline), molecular sieves, or an inorganic base (such as calcium carbonate or sodium bicarbonate) or a silylated derivative of acetamide [such as trimethylsilyl acetamide or N,O-bis(trimethylsilylacetamide)] or an oxirane, which binds hydrogen halide liberated in the acylation reaction. The oxirane is preferably a $(C_{1-6})$-1,2-alkylene oxide such as ethylene oxide or propylene oxide. The acylation reaction using an acid halide may be carried out at a temperature in the range −50° C. to +50° C., preferably −20° C. to +20° C., in aqueous or non-aqueous media such as water, acetone, tetrahydrofuran, ethyl acetate, dimethylacetamide, dimethylformamide, acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate. Preferred solvents include tetrahydrofuran, and anhydrous chlorinated hydrocarbons, especially dichloromethane.

Acids of formula (IX) may be prepared by the general method described in GB 1 508 064.

The acid halide may be prepared by reacting the acid (IX) or a salt or suitable derivative thereof with a halogenating (e.g. chlorinating or brominating) agent such as phosphorus pentachloride, phosphorus oxychloride, thionyl chloride, oxalyl chloride, or phosgene.

Suitable derivatives of the acid (IX) which may be employed in the above process include labile esters such as silyl esters. Suitable silyl esters include, for example, tri$(C_{1-6})$alkyl silyl esters, especially the trimethylsilyl ester.

Alternatively, the N-acylating derivative of the acid (IX) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric, phosphorous, and phosphinic acids) or aromatic or aliphatic sulphonic acids (such as p-toluenesulphonic acid or methanesulphonic acid). When a symmetrical anhydride is employed, the reaction may be carried out in the presence of 2,6-lutidine as catalyst.

Alternative N-acylating derivatives of acid (IX) are the acid azide, or activated esters such as esters with 2-mercaptopyridine, cyanomethanol, p-nitrophenol, 2,4-dinitrophenol, thiophenol, halophenols, including pentachlorophenol, monomethoxyphenol, N-hydroxy succinimide, N-hydroxybenzotriazole, or 8-hydroxyquinoline; or amides such as N-acylsaccharins, N-acylthiazolidin-2-thione or N-acylphthalimides; or an alkylidene iminoester prepared by reaction of the acid (IX) with an oxime.

Other reactive N-acylating derivatives of the acid (IX) include the reactive intermediates formed by reaction in situ with a condensing agent such as a carbodiimide, for example, N,N'-diethyl-, di-n-propyl- or diisopropylcarbodiimide, N,N'-di-cyclohexylcarbodiimide, or N-ethyl-N'-[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxazolinium-3-sulphonate or N-t-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3.C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

A further method of forming the N-acylating derivative of the acid (IX) is to treat the acid of formula (IX) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (IX) so derived may then be caused to react with a compound of formula (VIII). The acylation reaction may conveniently be carried out at −40° to +30° C., if desired in the presence of an acid binding agent such as pyridine, trimethylsilylacetamide or N,O-bis(trimethylsilylacetamide). A catalyst such as 4-dimethylaminopyridine may optionally also be added. A preferred solvent for the above acylation reaction is dichloromethane.

The compounds of formula (VIII) herein which are, inter alia, intermediates for the compounds of formula (I) as hereinbefore defined may be prepared by reacting a compound of formula (X) or acid addition salt thereof:

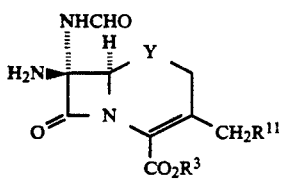

wherein $R^3$, $R^{11}$, and Y are as hereinbefore defined, with a compound of the formula (VI) as hereinbefore defined;

with the proviso that when $R^{11}$ is an acyloxy group, the group $CO_2R^3$ must be in the free acid form or a salt thereof;

and thereafter if necessary carrying out one or more of the following steps:

i) converting each or any one of the groups $R^3$, $R^4$ and $R^5$ into a different groups $R^3$, $R^4$ and $R^5$;

ii) removing any protecting group; or iii) converting the product into a salt.

The compounds of formula (I) may also suitably be prepared by a process which process comprises treating a compound of formula (XI):

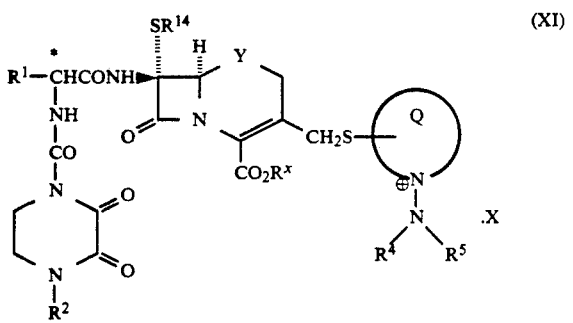

wherein $R^1$, $R^2$, $R^4$, $R^5$, ring Q, X, Y and * are as hereinbefore defined and wherein any reactive groups may be protected; $R^x$ is a readily removable carboxy protecting group; and $R^{14}$ is $(C_{1-6})$alkyl, aryl or benzyl;

with a heavy metal ion such as mercury, silver, thallium, lead or copper; and thereafter in situ with a nucleophilic derivative of formamide as described in EP-A 0 115 405 (to Beecham Group plc); and thereafter, if necessary, carrying out one or more of the following steps:

i) converting the group $R^x$ into a group $R^3$;

ii) converting either one or both of the groups $R^4$ and $R^5$ into a different group $R^4$ and $R^5$;

iii) removing any protecting groups; or iv) converting the product into a salt.

Suitable groups for $R^x$ include ester derivatives of the carboxylic acid as described hereinabove for the group $R^3$. The derivative is preferably one which may readily be cleaved.

The compounds of formula (I) may also be prepared by a process which process comprises treating a compound of formula (XII):

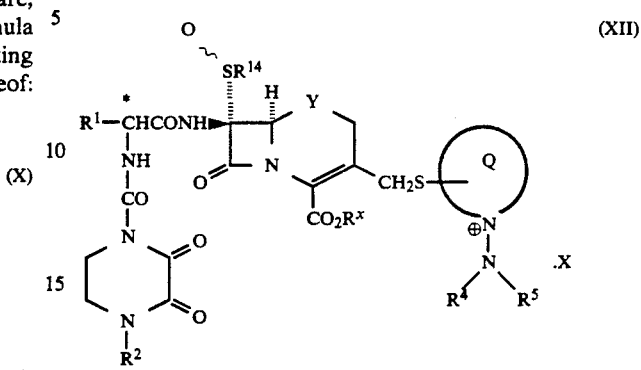

wherein $R^1$, $R^2$, $R^4$, $R^5$, ring Q, X, Y, *, $R^x$, and $R^{14}$ are as hereinbefore defined and wherein any reactive groups may be protected;

with a nucleophilic derivative of formamide; and thereafter, if necessary, carrying out one or more of the following steps:

i) converting the group $R^x$ into a group $R^3$;

ii) converting either one or both of the groups $R^4$ and $R^5$ into a different group $R^4$ and $R^5$;

iii) removing any protecting groups; or iv) converting the product into a salt.

The present invention further provides a process for the preparation of a compound of formula (I) which process comprises formylating a compound of formula (XIII):

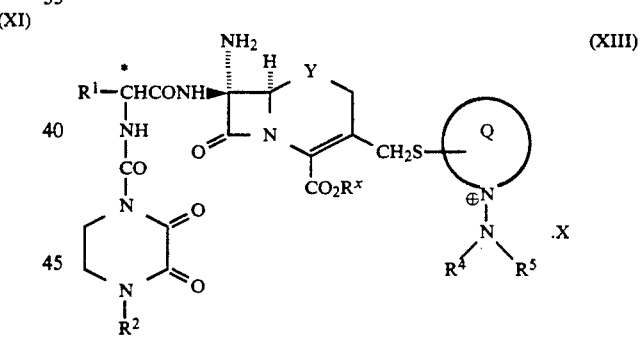

wherein X, Y, ring Q, $R^1$, $R^2$, $R^4$, $R^5$, $R^x$ and * are as hereinbefore defined and wherein any reactive groups may be protected; and thereafter, if necessary, carrying out one or more of the following steps:

i) converting the group $R^x$ into a group $R^3$;

ii) converting either one or both of the groups $R^4$ and $R^5$ into a different group $R^4$ and $R^5$;

iii) removing any protecting groups; or iv) converting the product into a salt.

Suitable formylating agents include the reagent 4-formyl-2-methyl-1,3,4-thiadiazolin-5-thione (see H. Yazawa and S. Goto, *Tetrahedron Letters*, 1985, 26, 3703–3706), or mixed anhydrides such as formic acetic anhydride. The reaction may suitably be carried out in a temperature in the range $-50°$ C. to $30°$ C. in an aprotic solvent such as, for example, dichloromethane, chloroform, dimethylformamide, tetrahydrofuran, hexamethylphosphoramide, or dimethylsulphoxide, in the presence of a tertiary base. A preferred tertiary base employed in the reaction is a base of the pyridine type, such as pyridine, lutidine or picoline.

Compounds of formula (XIII) may be prepared by analogy with processes disclosed in EP-A-0 071 395 (to Beecham Group p.l.c.).

It will be apparent from the above that a process for preparing compounds of formula (I) comprises formamidylating a compound of formula (XIV):

(XIV)

wherein L is $SR^{14}$, $SOR^{14}$ or $NH_2$; and X, Y, ring Q, $R^1$, $R^2$, $R^4$, $R^5$, $R^{14}$, $R^x$ and * are as hereinbefore defined.

As used herein the term 'formamidylating' denotes converting the group L into the group —NHCHO.

Compounds of formula (XIV) may be prepared by the treatment of compounds of formula (XV):

(XV)

wherein $R^1$, $R^2$, $R^{11}$, $R^x$, L, and * are as hereinbefore defined, with a compound of formula (VI), as hereinbefore defined.

Compounds of formula (XV) may be prepared by analogy with processes described in EP-A-0 071 395 and EP-A-0 115 405 (to Beecham Group plc).

The compounds of formula (I) may also suitably be prepared by reacting a compound of formula (XVI):

(XVI)

wherein $R^1$, $R^3$, $R^4$, $R^5$, X, Y, ring Q, n, and * are as hereinbefore defined and the α-amino group in the 7β-side-chain is optionally substituted with a group which permits acylation to take place, and any reactive groups may be protected;

with an N-acylating derivative of an acid of formula (XVIII);

(XVII)

wherein $R^2$ is as hereinbefore defined and wherein any reactive groups may be protected; and thereafter, if necessary, carrying out one or more of the following steps:

i) converting each or any one of the groups $R^3$, $R^4$ and $R^5$ into another group $R^3$, $R^4$ and $R^5$.

ii) removing any protecting groups; or iii) converting the product into a salt.

The compounds of formula (XVI) herein which are inter alia intermediates for the compounds of formula (I) as hereinbefore defined may be prepared by reacting a compound of formula (VIII) with an N-acylating derivative of an acid of formula (XVIII):

$$R^1.\overset{*}{C}H.CO_2H \quad (XVIII)$$
$$\mid$$
$$NHR^{15}$$

wherein $R^1$ and * are as hereinbefore defined and $R^{15}$ is an amino-protecting group, and thereafter removing protecting group $R^{15}$.

Suitable amino-protecting groups $R^{15}$ are those well-known in the art which may be removed under conventional conditions without disruption of the remainder of the molecule.

Examples of amino-protecting groups for $R^{15}$ include benzyl optionally substituted in the phenyl ring by one or two substituents selected from ($C_{1-4}$)alkyl, ($C_{1-4}$)alkoxy, trifluoromethyl, halogen or nitro; ($C_{1-4}$)alkoxycarbonyl optionally substituted by a phenyl or biphenylyl group, for example tert-butoxycarbonyl or 1-methyl-1-(4-biphenylyl)ethoxycarbonyl; benzyloxycarbonyl optionally substituted as for benzyl above; allyloxycarbonyl; or trityl.

Compounds of formula (XVI) may also be prepared by reacting a compound of formula (VIII) with an N-acylating derivative of an acid of formula (XIX):

(XIX)

wherein $R^1$ and * are as hereinbefore defined; and thereafter converting the phthalimido group into an amino group by conventional methods.

Compounds of formula (XVI) may also be prepared by reacting a compound of formula (VIII) with an N-acylating derivative of an α-azido acid of formula (XX):

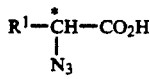

(XX)

wherein $R^1$ and * are as hereinbefore defined; followed by conversion of the azido group into an amino group by conventional methods, for example, by catalytic hydrogenation, or by reaction with triphenylphosphine followed by hydrolysis of the resultant phosphinimine.

In an alternative aspect, the resultant phosphinimine prepared as described above may be treated with an N-acylating derivative of an acid of formula (XVII) as hereinbefore defined to provide yet a further process for preparing compounds of formula (I). In this reaction the N-acylating derivative of the acid of formula (XVII) is preferably the acid chloride.

Compounds of formula (V) may be prepared by reacting a compound of formula (X) as hereinbefore defined, or a salt thereof; in which $R^{11}$ is halo, the 7β-amino group is optionally substituted with a group which permits acylation to occur, and any reactive groups may be protected; with an N-acylating derivative of an acid of formula (IX), as hereinbefore defined, and thereafter, if necessary, carrying out one or more of the following steps:

i) converting a group $R^3$ into another group $R^3$;
ii) removing any protecting groups; or
iii) converting the product into a salt.

Compounds of formula (X) may be prepared by a process which process comprises treating a compound of the formula (XXI):

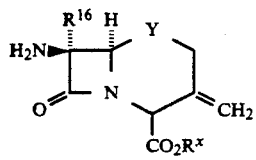

(XXI)

in which $R^{16}$ is a formamido group, or a group readily convertible to a formamido group, $R^x$ and Y are as hereinbefore defined, the 7β-amino group is optionally substituted with an amino protecting group, and any reactive groups may be protected;

with a halogenating agent and a base and, thereafter, if necessary or desired, carrying out one or more of the following steps in any suitable order:

(i) converting the group $R^{11}$ into a different group $R^{11}$;
(iii) converting the group $R^{16}$ into a formamido group;
(iii) converting the group $R^x$ into a group $R^3$;
(iv) removing any protecting groups; or
(v) converting the product into a salt.

The halogenating agent may be any compound conventionally used for the electrophilic addition of a halogen atom. Suitable such reagents include those described in 'Advanced Organic Chemistry' by Jerry March (John Wiley and Sons, New York, 1985). Preferred reagents are chlorine or t-butylhypochlorite for chlorination, bromine or diethyldibromomalonate for bromination and iodine for iodination.

The use of diethyldibromomalonate as a brominating agent is described by van der Wolf and Pabon in *J. Royal Netherlands Chem. Soc.*, 1977, 96, 72.

The base used in combination with the halogenating agent may be any strong, non-nucleophilic base. Suitable such reagents include those described in 'Advanced Organic Chemistry' (op.cit.). Preferably the base is 1,5-diazabicyclo[4.3.0]non-5-ene (DBN) or 1,8-diazabicyclo[5.4.0]undec-7-ene (DBU).

Whilst the base may be used in a stoichiometric amount, it is found preferable, especially when used in conjunction with diethyldibromomalonate, to use the base in a catalytic amount, for instance 0.1 to 50 mol %, more preferably 1 to 20 mol %, with respect to compound of the formula (XXI).

The reaction is normally performed at low temperature, for example between −100° C. and +10° C., preferably −85° C. to −50° C., most preferably −78° C., in an inert organic solvent, for instance tetrahydrofuran, N,N-dimethylformamide, 1,2-dimethoxyethane or dichloromethane, or mixtures thereof. Preferably the solvent is anhydrous.

When used herein, the term 'group readily convertible to a formamido group' denotes an amino group or a group $SR^{14}$ or $SOR^{14}$ wherein $R^{14}$ is as hereinbefore defined.

Such groups may be converted to formamido by methods known in the art, for example those described in EP-A-0 071 395 and EP-A-0 115 405A (to Beecham Group plc).

Preferably $R^{16}$ is a formamido group.

It will be appreciated that the treatment of compounds of formula (XXI) with a halogenating agent as hereinbefore described is more generally applicable to compounds of formula (XXI) wherein the 7β-amino group is substituted with an acyl group, preferably one that is used in antibacterially active penicillins and cephalosporins, to give a compound corresponding to that of formula (X) in which the 7β-amino is substituted with an acyl group, as hereinbefore defined, for instance a compound of formula (V), as hereinbefore defined.

Compounds of formula (XXI) can be prepared from compounds of formula (XXII):

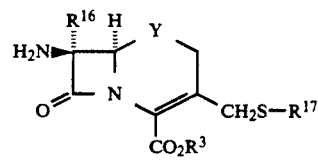

(XXII)

in which $R^3$ and $R^{16}$ are as hereinbefore described and $R^{17}$ is heterocyclyl, by analogy with the methodology described by Guest et al in *J. Chem. Soc.*, Perkin I, 1985, 45. Compounds of formula (XXII) may be prepared by methods known in the art, for instance those described in EP-A-0 071 395, and EP-A-0 115 405.

Alternatively a compound of formula (X) wherein $R^{11}$ is chloro or acetoxy may be prepared according to the process described by Kamachi et al in *Journal of Antibiotics*, 1990, XLIII (7), 820-829.

Compounds of formula (VIII), (XIV) and (XVI) which may be represented by the general formula (XXIII):

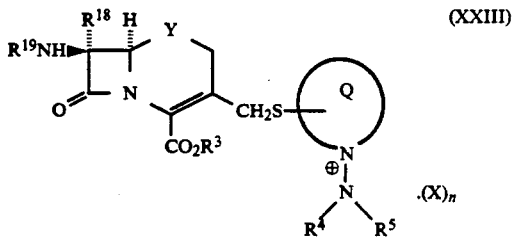

(XXIII)

in which R$^{18}$ is L and R$^{19}$ the moiety:

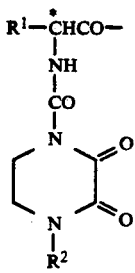

in which R$^1$ and R$^2$ are as hereinbefore defined, and n is 1; or

R$^{18}$ is NHCHO, and R$^{19}$ is hydrogen or the moiety:

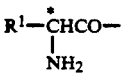

in which R$^1$ and * are as hereinbefore defined; are novel and valuable intermediates.

Accordingly, a further aspect of the invention provides compounds of formula (XXIII) as hereinbefore defined.

Compounds of the formula (I) in which Y is sulphur, —SO—, or —SO$_2$— may be inter-converted by methods known in the art.

The compounds of sub-formulae (Ia), (Ib), and (Ic) may be prepared by similar processes to those described hereinabove as suitable for the preparation of a compound of the formula (I), except that each process for the preparation of the compound of formulae (Ia), (Ib) or (Ic) further comprises, if necessary, the step of converting the product into a pharmaceutically acceptable salt or pharmaceutically acceptable in vivo hydrolysable ester.

Conversion of compounds of formula (Ib) into compounds of formula (Ic) and vice-versa may be readily carried out by conventional methods. For instance, compounds of formula (Ic) may be obtained from compounds of formula (Ib) by treatment with a dilute mineral acid such as hydrochloric acid.

Quaternary salts within formula (Ic) may also be prepared by salt exchange in a conventional manner, for example by means of an ion-exchange resin.

The antibiotic compounds of the present invention are active against a wide range of Gram-negative and Gram-positive organisms including *E.coli* such as, for example ESS, JT4, JT425 and NCTC 10418; Pseudomonas Spp. such as *Ps.aeruqinosa* for example 10662 and Dalgleish; *Serratia marcescens* US32; *Klebsiella aerogenes* A; *Enterobacter cloacae* N1; *P.mirabilis* such as, for example C977 and 889; *P.morganii; P.rettgeri; B.subtilis; Staph. aureus* such as, for example Oxford and Russell.

The following Examples illustrate the preparation of the compounds of the present invention.

PREPARATION 1

1-(3,4-Dihydroxybenzoylamino)-4-thiopyridone

4-Thiopyranone (0.10 g, 0.089 mmol) in N,N-dimethylformamide (5 ml) was treated with 3,4-dihydroxybenzhydrazide (0.12 g, 0.71 mmol) and stirred at room temperature for 24 h. The solvent was evaporated under reduced pressure and the residue was triturated with dichloromethane. Filtration and drying gave the title compound (0.105 g, 51%); $v_{max}$ (KBr) 1662 and 1606 cm$^{-1}$; $\delta_H$ (CD$_3$)$_2$SO] 6.85 (1H, d, J 8 Hz), 7.17 (2H, d, J 7 Hz), 7.22–7.39 (2H, m), 7.67 (2H, d, J 7 Hz), and 9.0–9.1 (3H, m); m/z (positive xenon F.A.B.; thioglycerol) MH+ 263.

PREPARATION 2

1-(Dimethylamino)-4-thiopyridone

4-Thiopyranone (0.112 g, 1.0 mmol) in N,N-dimethylformamide (2.0 ml) was treated with 1,1-dimethylhydrazine (0.76 ml, 10 mmol) and stirred at room temperature for 3 h. The solvent was evaporated under reduced pressure and the residue chromatographed on silica gel 60 (<230 mesh ASTM) eluting with ethanol, dichloromethane (9:1) to give the title compound (0.069 g, 45%); $\delta_H$(CDCl$_3$) 2.88 (6H, S), and 7.55 (4H, s); M+ 154.

PREPARATION 3

1-(Pyrrolidin-1-yl)-4-thiopyridone

1-Aminopyrrolidine hydrochloride (0.25 g, 2.0 mmol) was suspended in diethyl ether and treated with a solution of sodium hydroxide (0.08 g, 2.0 mmol) in water (5 ml). The organic layer was separated, dried over magnesium sulphate and evaporated carefully under reduced pressure.

4-Thiopyranone (0.112 g, 1.0 mmol) in ethanol (5 ml) was treated with 1-aminopyrrolidine (0.17 g, 2.0 mmol) in ethanol (2 ml) and stirred at room temperature for 2 h, then 60° C. for 3 h. A further quantity of 1-aminopyrrolidine (0.17 g, 2.0 mmol), liberated from the hydrochloride as described above, was added to the reaction mixture and heating continued at 60° C. for 2 h. The solution was allowed to cool, then evaporated to dryness under reduced pressure. Chromatography on silica gel 60 (<230 mesh ASTM) eluting with ethanol, dichloromethane mixtures gave the title compound (0.051 g, 32%); $v_{max}$ (KBr) 1604 cm$^{-1}$; $\delta_H$ (CDCl$_3$) 1.97 (4H, m), 3.20 (4H, m), and 7.48 (4H, s); M+ 180.

PREPARATION 4

1-(N-Benzyl-N-methylamino)-4-thiopyridone

Methylhydrazine (0.1 ml, 2.0 mmol) in dichloromethane (5 ml) was treated dropwise with a solution of benzyl bromide (0.12 ml, 1.0 mmol) in dichloromethane (2 ml). After addition was complete the mixture was stirred for 10 min. and evaporated to dryness under reduced pressure. The residue was diluted with brine (5 ml) and ethyl acetate (5 ml). The organic phase was separated, dried over magnesium sulphate and evaporated to dryness under reduced pressure to give N-benzyl-N-methylhydrazine (0.082 g, 60%); $v_{max}$ (CH$_2$Cl$_2$)

1650 cm$^{-1}$; δ$_H$(CDCl$_3$) 2.49 (3H, s), 3.41 (2H, s), 3.60 (2H, s), and 7.27 (5H, s).

4-Thiopyranone (0.070 g, 0.62 mmol) was added to N-benzyl-N-methylhydrazine (0.082 g, 0.6 mmol) in ethanol (5 ml). The mixture was heated at reflux for 4 h, then allowed to cool. Chromatography on silica gel 60 (<230 mesh ASTM) eluting with ethanol, dichloromethane mixtures gave the title compound (0.071 g, 51%); ν$_{max}$(CH$_2$Cl$_2$) 1610 cm$^{-1}$; δ$_H$(CDCl$_3$) 2.83 (3H, s), 4.02 (2H, s), and 7.18 (9H, s).

PREPARATION 5

1-(N-Carbamoylmethyl-N-methylamino)-4-thiopyridone

Methylhydrazine (0.2 ml, 4.0 mmol) in dichloromethane (5 ml) was treated dropwise with a solution of iodoacetamide (0.37 g, 2.0 mmol) in tetrahydrofuran (3 ml). After addition was complete the mixture was stirred for 1 h. The supernatant was decanted from the colourless oil which had separated from the reaction mixture. The oil was dissolved in ethanol (5 ml) and a portion (2 ml) of this solution added to 4-thiopyranone (0.112 g, 1.0 mmol) in ethanol (3 ml). The reaction mixture was heated at reflux for 4 h, cooled and evaporated to dryness under reduced pressure. The residue was chromatographed on silica gel 60 (<230 mesh ASTM) eluting with ethanol, dichloromethane mixtures to give the title compound (0.03 g, 15%); δ$_H$ (CDCl$_3$+CD$_3$OD) 3.04 (3H, s), 3.92 (2H, s), 7.38–7.62 (2H, m), and
7.9–8.1 (2H, m).

PREPARATION 6

1-(Methylamino)-4-thiopyridone (a) t-Butyl 1-methylhydrazinecarboxylate

N-Methylhydrazine (1.6 ml; 0.03 mol) in dichloromethane (20 ml) was treated with di-t-butyl dicarbonate (6.6 g; 0.03 mol) in dichloromethane (25 ml) dropwise, and stirred for 90 minutes. The mixture was decanted from the sticky residue and evaporated to minimum volume twice from dichloromethane and once from dichloromethane/toluene to give the title compound (4 g, 97% ); δH (CDCl$_3$) 1.47 (9H, s), and 3.03 (3H, s).

(b) 1-[N-(t-Butyloxycarbonyl)-N-methylamino]-4-thiopyridone t-Butyl 1-methylhydrazinecarboxylate (0.5 g; 3.4 mmol) and 4-thiopyrone (0.34 g; 3 mmol) in ethanol (20 ml) were refluxed for 24 hours. The solution was evaporated to dryness and the product purified by chromatography on silica gel eluting with mixtures of hexane and ethyl acetate to give the title compound (0.55 g, 76%); δH (CDCl$_3$) 1.47 (9H, s), 3.37 (3H, s), 7.19 and 7.32 (4H, ABq, J 7Hz); λ$_{max}$ (EtOH) 356 nm (E 29050 dm$^3$ mol$^{-1}$ cm$^{-1}$) (Found: M$^+$, 240.0945, C$_{11}$H$_{16}$N$_2$O$_2$S requires M, 240.0932).

(c) 1-(Methylamino)-4-thiopyridone

1-[N-(t-Butyloxycarbonyl)-N-methylamino]-4-thiopyridone (1 g; 4.16 mmol) in dichloromethane (40 ml) was treated with trifluoroacetic acid (5 ml) and stirred for 2½ hours. On completion of the reaction the mixture was evaporated to dryness and the residue dissolved in ethyl acetate. The product was extracted into water maintained at pH 6.8 with sodium bicarbonate. The water was evaporated to low volume and then the product absorbed onto silica gel by evaporation. The product was then purified by chromatography on silica gel eluting with mixtures of ethanol in dichloromethane to give the title compound (0.4 g, 67%) ν$_{max}$ (KBr) 1685, 1605, 1523 and 1108 cm$^{-1}$; δH (CDCl$_3$) 2.95 (3H, d, J 6Hz), 5.46 (1H, q, J 6Hz), and 7.34 (4H, s); M$^+$ 140.

PREPARATION 7

1-(N-Acetyl-N-methylamino)-4-thiopyridone 1-(Methylamino)-4-thiopyridone(0.21 g, 1.5 mmol) in dichloromethane (20 ml) was treated with triethylamine (0.21 ml, 1.5 mmol) and then acetic anhydride (0.15 ml, 1.6 mmol) and stirred for 5 minutes. The product was obtained by purification on silica gel eluting with 2% ethanol in dichloromethane (0.17 g, 62%); ν$_{max}$ (CH$_2$Cl$_2$) 1700 and 1615cm$^{-1}$; δh (CDCl$_3$) 2.02 (3H, s), 3.40 (3H, s), 7.08 (2H,d, J 7.5Hz), and 7.41 (2H, d, J 7.5Hz); M$^+$ 182.

PREPARATION 8

1-(N-Formyl-N-methylamino)-4-thiopyridone 1-(Methylamino)-4-thiopyridone (0.2 g 1.43 mmol) in dichloromethane at 0° C. was treated with triethylamine (0.2 ml; 1.43 mmol) and then acetic formic anhydride (0.11 ml; 1.57 mmol) and stirred for 10 minutes. The product was obtained by purification on silica gel eluting with mixtures of ethanol in dichloromethane (0.175 g, 73%). The product was a mixture of rotamers confirmed by variable temperature n.m.r. coalescence occuring by 360K; δH [(CD$_3$)$_2$SO] 3.26, 3.43 (3H, 2s), 7.17 and 7.84, 7.20 and 7.65 (4H, 4d, J 7.5Hz), 8.31, 8.41 (1H, 2s).

PREPARATION 9

1-[N-(4-Nitrobenzoyl)-N-methylamino]-4-thiopyridone

1-Methylamino-4-thiopyridone (50 mg; 0.36 mmol) in dichloromethane (2 ml) was treated with triethylamine (0.05 ml, 0.36 mmol) followed by p-nitrobenzoyl chloride (66 mg, 0.36 mmol) dissolved in dichloromethane (5 ml) for 30mins. Chromatography on silica gel eluting with methanol and dichloromethane mixtures gave the title compound (92 mg, 89%); δ$_H$[(CD$_3$)$_2$SO] 3.36 (3H, s), 7.8 (2H, broad), 7.96 (2H, s), 7.99 (2H, s), and 8.35 (2H, broad); M$^+$ 289.

PREPARATION 10

1[N-(4-Methoxybenzoyl)-N-methylamino]-4-thiopyridone

Reaction of 1-methylamino-4-thiopyridone (78 mg, 0.56 mmol), triethylamine (56 mg, 0.56 mmol) and p-anisoyl chloride (95 mg, 0.56 mmol) in tetrahydrofuran (25 ml) for 30 mins followed by silica gel chromatography eluting with mixtures of methanol and dichloromethane gave the title compound (148 mg, 96%); ν$_{max}$ (CHCl$_3$) 1670 and 1615 cm$^{-1}$; δ$_H$(CDCl$_3$) 3.49 (3H, s), 3.80 (3H, s), 6.86 (2H, d, J Hz), 7.11 and 7.3 (4H, ABq, J 7Hz), and 7.44 (2H, d, J 8Hz); M$^+$ 274.

PREPARATION 11

1-[N-(2-Furoyl)-N-methylamino]-4-thiopyridone

Reaction of 1-methylamino-4-thiopyridone (90 mg, 0.64 mmol) and triethylamine (0.09 ml, 0.64 mmol) and 2-furoyl chloride (84 mg, 0.64 mmol) in dichloromethane (15 ml) for 30 mins followed by silica gel chromatography eluting with mixtures of methanol, dichloromethane gave the title compound (138 mg, 92%); $v_{max}$ (CHCl$_3$) 1660 and 1615 cm$^{-1}$; $\delta_H$ (CDCl$_3$/CD$_3$OD) 3.55 (3H, s), 6.46 (1H, dd, J 2, and 4H), 6.9 (1H, d, J 4Hz), 7.29 (2H, s), 7.38 (2H, s), and 7.45 (1H, bs); M+ 234.

PREPARATION 12

1-[N-(2-Hydroxyethyl)-N-methylamino]-4-thiopyridone

2-Hydroxyethylhydrazine (0.135 g, 2.0 mmol) in diethylether (5 ml) was treated dropwise with a solution of methyl iodide (0.06 ml, 1.0 mmol) in diethylether (2 ml). The reaction mixture was stirred for 0.5 h, during which time a colourless oil separated from the solution. The solution was removed from the oil and evaporated under reduced pressure. The residue was dissolved in ethanol (5 ml) and 4-thiopyranone (0.112 g, 1.0 mmol) added. The mixture was heated at reflux for 2 h, evaporated under reduced pressure and chromatographed on silica gel 60, eluting with ethanol, dichloromethane (1:19) to give the title compound (0.028 g, 9%); $\delta_H$ (CDCl$_3$) 2.95 (3H, s), 3.06–3.39 (2H, m), 3.54–3.85 (2H, m), and 7.33–7.70 (4H, m); M+ 184.

PREPARATION 13

1-(t-Butyloxycarbonylamino)-4-thiopyridone t-Butylcarbazate (0.13 g, 1.0 mmol) and 4-thiopyranone (0.11 g, 1.0 mmol) were heated at reflux in ethanol for 2 h. The mixture was allowed to cool, diluted with acetone, then evaporated under reduced pressure. Chromatography on silica gel 60 eluting with ethanol, dichloromethane (1:19) gave the title compound containing traces of unreacted t-butylcarbazate (0.49 g); $v_{max}$(KBr) 1745, 1611, and 1503 cm$^{-1}$; $\delta_H$(CDCl$_3$) 1.51 (9H, s), and 7.33 (4H, s); M+ 226.

PREPARATION 14

1-[N-(t-Butyloxycarbonyl)-N-(t-butyloxycarbonylmethyl)amino]-4-thiopyridone (a) 1-(t-Butyloxycarbonylamino)-4-pyridone 4-Pyranone (1 g, 10.4 mmol) and t-butylcarbazate (1.32 g, 10 mmol) were heated at reflux in ethanol for 48 h. The solvent was gradually allowed to distil from the mixture and the residue was chromatographed on silica gel 60, eluting with ethanol, dichloromethane (1:19) to give the title compound (1.16 g, 50%); $v_{max}$(KBr) 1723, 1630, and 1550 cm$^{-1}$; $\delta_H$ 1.54 (9H, s), 6.47 (2H, d), and 7.60 (2H, d); M+ 210.

(b) 1-[N-(t-Butyloxycarbonyl)-N-(t-butyloxycarbonylmethyl)amino]-4-pyridone 1-(t-Butyloxycarbonyl)amino-4-pyridone (0.057 g, 0.25 mmol) in N,N-dimethylformamide (5 ml) was treated successively with potassium carbonate (0.035 g, 0.25 mmol) and t-butyl bromoacetate (0.04 ml, 0.25 mmol). The reaction mixture was stirred for 0.5 h, evaporated under reduced pressure and chromatographed on silica gel 60 eluting with ethanol, dichloromethane (1:19) to give the title compound containing traces of solvent (0.09 g); $v_{max}$ (CH$_2$Cl$_2$) 1740, 1735 (sh), 1635, and 1590 cm$^{-1}$; $\delta_H$ (CDCl$_3$) 1.47 (9H, s), 1.51 (9H, s), 4.33 (2H, s), 6.37 (2H, d), and 7.70 (2H, d); M+ 324.

(c) 1-[N-(t-Butyloxycarbonyl)-N-(t-butyloxycarbonylmethyl)amino]-4-thiopyridone

The product from (b) (0.09 g, from 0.25 mmol) in toluene (5 ml) was treated with Lawesson's Reagent (0.057 g, 0.14 mmol). The mixture was heated at 80° C. for 5 mins, allowed to cool, then chromatographed on silica gel 60 eluting with ethanol, dichloromethane mixtures to give the title compound (0.081 g, 95%); $v_{max}$ (CH$_2$Cl$_2$) 1740, 1615, and 1115 cm$^{-1}$; $\delta_H$ (CDCl$_3$) 1.49 (9H, s), 1.72 (9H, s), 4.41 (2H, s), and 7.42 (4H, s); M+ 340.

PREPARATION 15

1-Amino-4-thiopyridone 1-(t-Butyloxycarbonylamino)-4-thiopyridone (1.12 g, 8.9 mmol) in dichloromethane (150 ml) was treated with trifluoroacetic acid (15 ml, 1.95 mol). The mixture was stirred for 1.5 h, then evaporated to low volume (ca. 30 ml) under reduced pressure. The solution was added to diethyl ether (150 ml) and the precipitate filtered off and dried to give the title compound (0.50 g, 80%), $v_{max}$ (KBr) 1684 and 1624 cm$^{-1}$; $\delta_H$[(CD$_3$)$_2$SO] 6.80 (2H, s), 7.11 (2H, d, J 7Hz), and 7.54 (2H, d, J 7Hz); M+126.

PREPARATION 16

1-(Diphenylamino)-4-thiopyridone

Diphenylhydrazine hydrochloride (0.11 g, 0.5 mmole) in diethylether (50 ml) was treated with 5N NaOH (20 ml). The mixture was shaken and the organic phase was separated, dried over magnesium sulphate, filtered and the filtrate evaporated under reduced pressure. The product in ethanol (5 ml) was treated with 4-thiopyranone (0.112 g, 1.0 mmol) and stirred under reflux for 18 h. The solvent was evaporated under reduced pressure and the residue chromatographed on silica gel 60 (<230 Mesh ASTM) eluting with ethanol, dichloromethane (1:9) to give the title compound (0.02 g, 22%).

PREPARATION 17

1-(Hexahydro-1H-azepin-1-yl)-4-thiopyridone

1-Aminohomopiperidine (0.116 ml, 1.0 mmole) in ethanol (5 ml) was treated with 4-thiopyranone (0.168 g, 1.5 mmole) and refluxed under argon for 3.5 h. The solvent was evaporated under reduced pressure and the residue chromatographed on silica gel 60 (<230 Mesh ASTM) eluting with ethanol, dichloromethane (1:9) to give the title compound (0.155 g, 79%).

PREPARATION 18

1-[4-(2-Hydroxyethyl)piperazin-1-yl-4-thiopyridone

1-Amino-4-(2-hydroxyethyl)piperazine (0.145 g, 1.0 mmole) in ethanol (5 ml) was treated with 4-thiopyranone (0.112, 1.0 mmole) and heated at reflux under argon for 6.0 h. The solvent was evaporated under reduced pressure and the residue chromatographed on silica gel 60 (<230 Mesh ASTM) eluting with ethanol, dichloromethane (1:4) to give the title compound (0.09 g, 38%).

PREPARATION 19

1-(Morpholin-4-yl)-4-thiopyridone

4-Aminomorpholine (0.1 ml, 1.0 mmol) in ethanol (5 ml) was treated with 4-thiopyranone (0.14 g, 1.25 mmol)

and heated at reflux under argon for 3½ h. The solvent was evaporated under reduced pressure and the residue chromatographed on silica gel 60 (<230 Mesh ASTM) eluting with ethanol, dichloromethane (1:9) to give the title compound (0.089 g, 45%).

PREPARATION 20

1-[N-[3,4-bis(4-Methoxybenzyloxy)benzoyl]-N-methylamino]-4-thiopyridone a) 4-Methoxybenzyl 3,4-bis(4-methoxybenzyloxy)benzoate 3,4-Dihydroxybenzoic acid (3.08 g, 0.02 mol) was dissolved in N,N-dimethylformamide (50 ml) and treated with 4-methoxybenzyl chloride (10 ml, 0.07 mol) and potassium carbonate (10 g, 0.07 mol). The mixture was warmed to 60° C. for 6 h and then stirred overnight. The mixture was partitioned between water and ethyl acetate. The organic phase was washed exhaustively with water and then the product was purified on silica gel 60 eluting with mixtures of ethyl acetate and hexane to give the title compound (6.48 g, 63%).

b) 3,4-bis(4-Methoxybenzyloxy)benzoic acid

4-Methoxybenzyl 3,4-bis(4-methoxybenzyloxy)benzoate (6.48 g, 0.013 mol) was suspended in ethanol and treated with 2.5N aqueous sodium hydroxide solution (7.6 ml, 0.015 mol). The mixture was warmed to 60° C. for 4 h. The mixture was evaporated to low volume and then partitioned between water and ethyl acetate. The aqueous layer was washed again with ethyl acetate and then acidified and extracted into ethyl acetate. As the ethyl acetate solution was concentrated the product precipitated from solution and was filtered off to give the title compound (4.36 g, 87%).

c) N-[3,4-bis(4-Methoxybenzyloxy)benzoyl]-N-methylhydrazine 3,4-bis-(4-Methoxybenzyloxy)benzoic acid (0.792 g, 2.0 mmol) was dissolved in dichloromethane (20 ml) and treated with N,N-diisopropylethylamine (0.35 ml, 2.0 mmol). The solution was cooled to −40° C. and treated with methanesulphonyl chloride (0.15 ml, 2.0 mmol). The mixture was allowed to warm to room temperature for 10 minutes and then re-cooled to −40° C. and added to a solution of methylhydrazine (0.215 ml, 4 mmol) in dichloromethane (10 ml) at −40° C. The mixture was allowed to warm to room temperature for 1.5 h and then evaporated to dryness under reduced pressure. The residue was dissolved in ethyl acetate which was washed with water and brine. Evaporation of the solvent gave the title compound (0.823 g, 94%); $\delta_H$(CDCl$_3$) 3.08 (3H, s), 3.74 (6H, s), 4.25 (2H, brs), 5.03 (4H, s), and 6.70–7.40 (11H, m).

d) 1-[N-3,4-bis(4-Methoxybenzyloxy)benzoyl]-N-methylamino]-4-thiopyridone

N-[3,4-bis-(4-Methoxybenzyloxy)benzoyl]-N-methylhydrazine (0.80 g, 1.8 mmol) was heated at reflux in ethanol (60 ml) with 4-thiopyranone (0.224 g, 2.0 mmol) for 48 hours. After evaporation under reduced pressure, purification on silica gel 60 gave the title compound (0.404 g; 43%); $\nu_{max}$. (KBr) 1656, 1612, and 1513 cm$^{-1}$; δH (CDCl$_3$) 3.40 (3H, s), 3.88 (6H, s), 5.02 (2H, s), 5.07 (2H, s), 6.90–7.30 (7H, m), 6.85 (2H, d), J 9Hz), and 7.30 (2H, d, J 9Hz); M+ 516.

PREPARATION 21

1-[N-[3,4-bis(4-Methoxybenzyloxy)cinnamoyl]-N-methylamino]-4-thiopyridone a) N-[3,4-bis(4-Methoxybenzyloxy)cinnamoyl]-N-methylhydrazine

The title compound was obtained by the method of Preparation 20 (a)-(c) using 3,4-dihydroxycinnamic acid in place of 3,4-dihydroxybenzoic acid; $\delta_H$ (CDCl$_3$) 3.25 (3H, s), 3.86 (6H, s), 3.95 (2H, brs), 5.05 (4H, s), and 6.65–6.80 (13H, m).

b) 1-[N-[3,4-bis(4-Methoxybenzyloxy)cinnamoyl]-N-methylamino]-4-thiopyridone N-[3,4-bis(4-Methoxybenzyloxy)cinnamoyl]-N-methylhydrazine (0.225 g, 0.54 mol) in ethanol (15 ml) containing 4-thiopyranone (0.056 g, 0.48 mol) was heated at reflux for 96 h. Purification on silica gel 60 eluting with mixtures of ethyl acetate and hexane gave the title compound (0.86 g, 35%); $\delta_H$(CDCl$_3$) 3.36 (3H, s), 3.74 (6H, s), 4.98 (2H, s), 5.02 (2H, s), 5.94 (1H, d, J 15 Hz), 6.75–7.45 (15H, m), and 7.63 (1H, d, J 15 Hz).

PREPARATION 22

1-(2-Oxopyrrolidin-1-yl)-4-thiopyridone

1-Amino-2-oxopyrrolidine (0.184 g, 2 mmol) and 4-thiopyranone (0.224 g, 2 mol) were heated at reflux in ethanol (25 ml) under argon for 24 h. The volatiles were removed under reduced pressure and the residue chromatographed on silica gel 60, eluting with dichloromethane then mixtures of ethyl acetate and hexane, to give the title compound (0.227 g, 58%); $\nu_{max}$ (CH$_2$Cl$_2$) 1725 and 1612 cm$^{-1}$; $\delta_H$ (CDCl$_3$) 2.16–2.70 (4H, m), 3.87 (2H, t, J 7 Hz), 7.10–7.50 (4H, m). (Found: M+, 194.0512. C$_9$H$_{10}$N$_2$OS requires M, 194.0514).

PREPARATION 23

1-(2-Oxopiperidin-1-yl)-4-thiopyridone

1-Amino-2-oxopiperidine (0.228 g, 2 mol) and 4-thiopyranone (0.23 g, 2 mol) in ethanol (25 ml) were heated at reflux for 3.5 h. The volatiles were removed under reduced pressure and the residue chromatographed on silica gel 60, eluting with dichloromethane then ethyl acetate, to give the title compound (0.264 g, 68%); $\nu_{max}$ (CH$_2$Cl$_2$) 1690, 1610 and 1115 cm$^{-1}$; $\delta_H$ (CDCl$_3$) 1.80–2.30 (4H, m), 2.59 (2H, t, J 7 Hz), 3.81 (2H, t, J 7 Hz), and 7.15–7.40 (4H, m)(Found: M+208.0669. C$_{10}$H$_{12}$N$_2$OS requires M, 208.0670).

PREPARATION 24

1-[N-(t-Butyloxycarbonyl)-N-(prop-2-en-1-yl)amino]-4-thiopyridone a) 1-[N-(t-Butyloxycarbonyl)-N-(prop-2-en-1-yl)amino-4-pyridone 1-(t-Butyloxycarbonylamino)-4-pyridone (0.2 g, 0.94 mol) in N,N-dimethylformamide (3 ml) was treated successively with potassium carbonate (0.131 g, 0.95 mol) and allyl bromide (0.114 g, 0.94 mol). The reaction mixture was stirred for 1 h and evaporated under reduced pressure. Purification on silica gel 60 eluting with ethanol, dichloromethane (1:9) gave the title compound (0.185 g, 78%); $\delta_H$ (CDCl$_3$) 1.45 (9H, s), 4.25 (2H, d, J 7 Hz), 5.19–5.35 (2H, m), 5.78–5.97 (1H, m), 6.34 (2H, d, J 8 Hz), and 7.21 (2H, d, J 8 Hz), M+ 250.

b)
1-[N-(t-Butyloxycarbonyl)-N-(prop-2-en-1-yl)amino]-4-thiopyridone

The product of Example 24(a) (0.185 g, 0.74 mol) in toluene (15 ml) was treated with Lawesson's reagent (0.225 g, 0.56 mol) and heated at 80° C. for 0.5 h. The mixture was allowed to cool and chromatographed on silica gel 60 eluting with ethanol, dichloromethane n mixtures to give the title compound (0.09 g, 46%); $\delta_H$ (CDCl$_3$) 1.46 (9H, s), 4.27 (2H, d, J 7 Hz), 5.20–5.37 (2H, m), 5.77–5.97 (1H, m), 7.05 (2H, d, J 7 Hz), and 7.40 (2H, d, J 7 Hz); M+ 266.

PREPARATION 25

1-(t-Butyloxycarbonylamino)-2,3-cyclopenteno-4-thiopyridone a) 2,3-Cyclopenteno-4-thiopyranone 2,3-Cyclopenteno-4-pyranone (0.56 g, 4.12 mol) (G. Jäger, *Justus Liebigs Ann. Chem.*, 1976, 1689–1712) in toluene (30 ml) was heated at 80° C. with Lawessons reagent (1.67 g, 4.13 mol) under Argon and stirred for 40 minutes, then allowed to cool and chromatographed on silica gel 60 eluting with dichloromethane to give the title compound (0.506 g, 81%); $\delta_H$[(CD$_3$)$_2$CO] 2.0–2.16 (2H, m), 2.7–2.81 (2H, m), 2.81–3.0 (2H, m), 7.00 (1H, d, J 5.34), and 7.83 (1H, d, J 5.33); MH+ 153.

b)
1-(t-Butyloxycarbonylamino)-2,3-cyclopenteno-4-thiopyridone 2,3-Cyclopenteno-4-thiopyranone (0.125 g, 0.82 mol) in ethanol (8 ml) was treaated with t-butylcarbazate (0.108 g, 0.82 mol) and heated at reflux under Argon for 4 days. The solvent was evaporated under reduced pressure and the residue chromatographed on silica gel 60 eluting with ethanol, dichloromethane (1:9) to give the title compound (0.083 g, 38%); $\delta_H$(CDCl$_3$) 1.4–1.63 (9H, m), 2.05–2.20 (2H, m), 2.68–3.08 (4H, m), 7.04 (1H, d, J 7 Hz), and 7.11 (1H, d, J 7 Hz); M+ 266.

DESCRIPTION 1

Diphenylmethyl
7β-Amino-3-bromomethyl-7α-formamidoceph-3-em-4-carboxylate (a) Diphenylmethyl
7β-Amino-7α-formamido-3-methylenecepham-4-carboxylate Powdered ammonium chloride (1.25 g) and powdered thiourea (0.5 g) were added to a solution of diphenylmethyl 7β-amino-7α-formamido-3-[(1,3,4-thiadiazol-2- yl)thiomethyl]ceph-3-em-4-carboxylate in N,N-dimethylformamide (20 ml) at ca. −10° C. (ice/acetone bath) with stirring. After 5 min activated (freshly acid washed) zinc powder (1.5 g) was added in four portions over 3 min. After 25 min the mixture was filtered through Kieselguhr and the residue washed with ethyl acetate and water. Ethyl acetate (100 ml) and water (100 ml) was added to the combined filtrate and washings. The organic phase was separated and the aqueous phase re-extracted with ethyl acetate (50 ml). The combined organic extracts were washed with water (×5), then brine (×1), and dried over anhydrous magnesium sulphate, filtered and the filtrate evaporated. Purification by silica gel chromatography eluting with ethyl acetate/n-hexane furnished the title compound as a white foam (0.744 g; containing ca. 10% diphenylmethyl 7β-amino-7α-formamido-3-methyl-ceph-3-em).

(b) Diphenylmethyl
7β-Amino-3-bromomethyl-7α-formamidoceph-3-em-4-carboxylate

A solution of 1,8-diazabicyclo[5.4.0]undec-7-ene (24 mg) in dry tetrahydrofuran (5 ml) was added over 5 min to a solution of diphenylmethyl 7β-amino-7α-formamido-3-methylenecepham-4-carboxylate (prepared above)(739 mg) in dry tetrahydrofuran (30 ml) containing diethyl dibromomalonate (999 mg) at −70° C. under argon. After 25 min the mixture was added to a mixture of ethyl acetate (150 ml) and 5% (w/v) aqueous citric acid (100 ml). The phases were separated and the organic phase washed with water (3×100 ml), brine (100 ml), then dried (anhyd. MgSO$_4$), filtered and the filtrate evaporated to give a yellow solid. Trituration with dichloromethane (15 ml) followed by filtration provided the title compound (609 mg) as a white solid, m.p. 151°–153° C. (decomp.) (Found: C, 52.33; H, 4.00; N, 8.37; S, 6.50; Br, 15.59%. C$_{22}$H$_{20}$N$_3$O$_4$SBr requires C, 52.59; H, 3.98; N, 8.37; S, 6.38; Br, 15.94%). $\nu_{max}$ (KBr) 3370, 3280, 3150, 1795, 1720, and 1670 cm$^{-1}$; $\delta_H$ (250 MHz, d$_8$-THF) (major rotamer) 2.70 (2H, broad s, exch. D$_2$O), 3.46 and 3.58 (2H, ABq, J 16.8 Hz), 4.34 and 4.42 (2H, ABq, J 10.0 Hz), 5.21 (1H, s), 6.95 (1H, s), 7.1–7.6 (10H, m), 8.15 (1H, d, J 1.0 Hz, becomes s on D$_2$O exch.), and 8.17 (1H, broad s, exch. D$_2$O); m/z (positive xenon F.A.B.; 3-nitrobenzyl alcohol-NaOAc) MNa;, 524.

DESCRIPTION 2

Diphenylmethyl
[6R,7R]-7-[[R]-2-[(4-Ethyl-2,3-dioxopiperazin-1-yl)carbonylamino]-2-phenylacetamido]-7-formamido-3-(halomethyl)ceph-3-em-4-carboxylate

[R]-2-[(4-Ethyl-2,3-dioxopiperazin-1-yl)carbonylamino]-2-phenylacetic acid (1.3 g, 4.1 mmol) in dichloromethane (15 ml) was treated with N,N-dimethylformamide (1 drop) and oxalyl chloride (1.0 ml, 11.0 mmol). The reaction was stirred for 0.75 h, then evaporated under reduced pressure. The residue was dissolved in dichloromethane and evaporated to dryness. The resulting acid chloride was dissolved in dichloromethane (10 ml) and added dropwise to a solution of diphenylmethyl [6R,7R]-7-amino-3-bromomethyl-7-formamidoceph-3-em-4-carboxylate (1.0 g, 2.0 mol) in tetrahydrofuran (20 ml) with pyridine (0.24 ml, 3.0 mol). After addition was complete the mixture was stirred for 1 h, then evaporated under reduced pressure. The residue was dissolved in ethyl acetate (40 ml) and water (40 ml). The organic phase was separated and washed with dil. HCl (2×40 ml), sodium hydrogen carbonate solution (2×40 ml), brine (40 ml), dried over magnesium sulphate and evaporated, under reduced pressure. Chromatography on silica gel 60 (<230 mesh ASTM) eluting with ethanol, dichloromethane mixtures gave the title compound (1.16 g, 77%). During the course of the reaction some halogen exchange occurs and the product is obtained as a mixture of 3-chloromethyl and 3-bromomethyl derivatives the relative quantities varying with each preparation. The preparation described contained predominantly diphenylmethyl [6R,7R]-3-chloromethyl-7-[[R]-2-[(4-ethyl-2,3- dioxopiperazin-1-yl)carbonylamino]-2-phenylacetamido]-7-formamidoceph-3-em-4-carboxylate; $v_{max}$ (KBr) 1787, 1720, and 1684 cm$^{-1}$; $\delta_H$ [(CD$_3$)$_2$CO] 1.16 (3H, t, J 7 Hz), 3.17 and 3.34 (2H, ABq, J 17 Hz), 3.50 (2H, q, J 7 Hz), 3.68 (2H, m), 4.04 (2H, m), 4.54 (2H, s), 5.35 (1H, s), 5.74 (1H, ( d, J 7 Hz), 6.95 (1H, s), 7.14 - 7.69 (15H, m), 8.30 (1H, d, J 1 Hz), 8.54 (1H, s), 8.82 (1H, s), and 10.04 (1H, d, J 7 Hz); m/z (positive xenon F.A.B, 3-nitrobenzylalcohol, NaOAc) MNa+ 781.

DESCRIPTION 3

Diphenylmethyl [6R,7R]-[[R]-2-(3,4-Diacetoxyphenyl)-2-[(4-ethyl-2,3-dioxopiperazin-1-yl)carbonylamino]acetamido]-7-formamido-3-(halomethyl)ceph-3-em-4-carboxylate

[D]-2-(3,4-Diacetoxyphenyl)-2-[(4-ethyl-2,3-dioxopiperazin-1-yl)carbonylamino]acetic acid (1.0 g, 3.1 mmol) in dichloromethane (30 ml) was treated with N,N-dimethylformamide (1 drop) and oxalylchloride (0.5 ml, 6.2 mol). The reaction was stirred for 1 h and then evaporated under reduced pressure. The residue was dissolved in dichloromethane and evaporated to dryness. The resulting acid chloride was dissolved in dichloromethane (10 ml) and added dropwise to a solution of diphenylmethyl [6R,7R]-7-amino-3-(bromomethyl)-7-formamidoceph-3-em-4-carboxylate (0.7 g, 1.4 mol) in tetrahydrofuran (30 ml) with pyridine (0.17 ml, 2.1 mmol). After the addition was complete the mixture was stirred for 2 h, and then evaporated under reduced pressure. The residue was dissolved in ethyl acetate (40 ml) and water (40 ml). The organic phase was separated and washed with dilute hydrochloric acid (2×40 ml), sodium hydrogen carbonate solution (2×40 ml), brine (40 ml), dried over magnesium sulphate and evaporated under reduced pressure. Purification on silica gel 60 eluting with ethanol, dichloromethane mixtures gave the title compound (0.888 g, 73%); $\delta_H$[(CD$_3$)$_2$CO] 1.17 (3H, t, J 17 Hz), 2.27 (6H, s), 3.05 and 3.31 (2H, ABq, J 16 Hz), 3.51 (2H, m), 3.69 (2H, m), 4.04 (2H, m), 4.50 and 4.64 (2H, ABq, J 11 Hz), 5.35 (1H, s), 5.77 (1H, d, J 7 Hz), 6.95 (1H, s), 7.20–7.80 (13H, m), 8.31 (1H, s), 8.53 (1H, s), 8.91 (1H, s), and 10.10 (1H, d, J 6 Hz).

DESCRIPTION 4

Diphenylmethyl [6R,7R]-7-[R]-2-(3,4-dihydroxyphenyl)-2-[[(4-ethyl-2,3-dioxopiperazin-1-yl)carbonylamino]acetamido]-7-formamido]-3-(halomethyl)ceph-3-em-4-carboxylate

[R]-2-[(4-Ethyl-2,3-dioxopiperazin-1-yl)carbonylamino]2-[3,4-bis(trimethylsilyloxy)phenyl]acetyl chloride EP 0 219 926 (Beecham Group) (0.75 g, 1.5 mmol) in tetrahydrofuran (25 ml) was added dropwise to a stirred mixture of diphenylmethyl [6R,7R]-7-amino-3-(bromomethyl)-7-formamidoceph-3-em-4-carboxylate (0.50 g, 1.0 mol) and pyridine (0.08 ml, 1.0 mol) in dichloromethane (10 ml), tetrahydrofuran (5 ml). The reaction mixture was stirred for 3 h, diluted with water (1 ml), then evaporated to dryness. Purification on silica gel 60 eluting with ethanol, dichloromethane mixtures gave the title compound (0.65 g, 82%). Due to halogen exchange occurring during the reaction the product is obtained as a mixture of 3-chloromethyl and 3-bromomethyl derivatives. The preparation described contained predominantly diphenylmethyl [6R,7R]-3-(chloromethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate; $v_{max}$ (KBr) 1786, 1717, 1675, and 1611 cm$^{-1}$; $\delta_H$(CDCl$_3$+CD$_3$OD) 1.13 (3H, t, J 7 Hz), 2.98 and 3.11 (2H, ABq, J 17 Hz), 3.43 (4H, m), 3.91 (2H, m), 4.31 (2H, m), 5.25 (1H, s), 5.41 (1H, brs), 6.71–7.04 (4H, m), 7.12–7.60 (10H, m), 8.13 (1H, s), and 9.82 (1H, brs); m/z (positive xenon F.A.B., 3-nitrobenzylalcohol-sodium acetate) MNa+ 813.

EXAMPLE 1

[6R,7R]-3-[1-(3,4-Dihydroxybenzoylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate (a) Diphenylmethyl [6R,7R]-3-[1-(3,4-Dihydroxybenzoylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.15 g,0.19 mol) in dichloromethane (5 ml) was treated with 1-(3,4-dihydroxybenzoylamino)-4-thiopyridone (0.08 g, 0.31 mol) in N,N-dimethylformamide (2 ml). The reaction mixture was stirred at room temperature for 5 h. The solvent was removed under reduced pressure. The residue was dissolved in dichloromethane and chromatographed on silica gel 60 (<230 mesh ASTM) eluting with ethanol, dichloromethane mixtures to give the title compound (0.041 g, 24%); $v_{max}$ (KBr) 1787, 1713, 1676, and 1610 cm$^{-1}$; $\delta_H$(CDCl$_3$+CD$_3$OD) 1.22 (3H, t, J 7 Hz), 2.78 and 2.93 (2H, ABq, J 16 Hz), 3.62 (CD$_3$OH covering 4H, m), 4.04 (2H, m), 4.28 and 4.42 (2H, ABq, J 12.5 Hz), 5.25 (1H, s), 5.46 (1H, s), 6.83–6.98 (2H, m), 6.95 (1H, s), 7.17–7.56 (18H, m) 8.08 (2H, d), and 8.20 (1H, s); m/z (positive xenon F.A.B., thioglycerol) M+ 985.

(b) [6R,7R]-3-[1-(3,4-Dihydroxybenzoylamino)pyridinium-4-thiomethyl]-4-thiomethyl]-7-[[R]-2-[(4-ethyl-2,3-dioxopiperazin-1-yl)carbonylamino]-2-phenylacetamido]-7-formamidoceph-3-em-4-carboxylate Diphenylmethyl [6R,7R]-3-[1-(3,4-dihydroxybenzoylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate halide (0.055 g, 0.05 mol) was treated with trifluoroacetic acid (2 ml) and stirred for 10 mins. The mixture was evaporated to dryness under reduced pressure. The residue was diluted with toluene and evaporated under reduced pressure. Purification on Diaion HP 20SS resin eluting with water, acetone mixtures followed by lyophilisation gave the title compound (0.026 g, 59%); $v_{max}$ (KBr) 1774, 1709, 1676, and 1616 cm$^{-1}$; $\delta_H$ [D$_2$O+(CD$_3$)$_2$CO] 1.23 (3H, t, J 7 Hz), 3.14 and 3.51 (2H, ABq, J 17 Hz), 3.56 (2H, q, J 7 Hz), 3.76 (2H, m), 4.07 (2H, m), 4.33 and 4.45 (2H, ABq, J 14 Hz), 5.30 (1H, s), 5.61 (1H, s), 6.99 (1H, d, J 8 Hz), 7.3–7.7 (7H, m), 8.03 (2H, d, J 7 Hz), 8.19 (1H, s), and 8.51 (2H, m); m/z (positive xenon F.A.B; thioglycerol) MH+ 819, M Na+841.

EXAMPLE 2

[6R,7R]-3-[1-(Dimethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate

(a) Diphenylmethyl [6R,7R]-3-[1-(Dimethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Iodide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.2 g, 0.25 mol) in acetone (5 ml) was treated with sodium iodide (0.037 g, 0.25 mol) and stirred at room temperature for 1 h. The precipitated sodium chloride was removed by filtration and the filtrate evaporated under reduced pressure. The residual solid was dissolved in chloroform (2 ml) and treated with 1-(dimethylamino)-4-thiopyridone (0.068 g, 0.45 mol). The reaction mixture was stirred at room temperature for 3.5 h then evaporated under reduced pressure to give the title compound which was used without purification in the next reaction.

(b) [6R,7R]-3-[1-(Dimethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Diphenylmethyl [6R,7R]-3-[1-(dimethylamino)pyridinium-4-thiomethyl]-7-[[R]-2-[(4-ethyl-2,3-dioxopiperazin-1-yl)carbonylamino] -2-phenylacetamido]-7-formamidoceph-3-em-4-carboxylate iodide was treated with trifluoroacetic acid (2 ml) and stirred for 10 min. The reaction mixture was diluted with toluene and evaporated to dryness under reduced pressure. The residue was diluted with toluene and evaporated to dryness three times. Purification on Diaion HP 20SS resin eluting with water, acetone mixtures followed by lyophilisation afforded the title compound (0.10 g, 58%); $\nu_{max}$ (KBr) 1780, 1705, 1680, and 1605 cm$^{-1}$; $\delta_H$ (D$_2$O) 1.14 (3H, t, J 7 Hz), 2.90 and 3.35 (2H, ABq, J 17 Hz), 2.97 (6H, s), 3.45 (2H, q, J 7 Hz), 3.59-3.70 (2H, m), 3.96 (2H, m), 4.03 and 4.33 (2H, ABq, J 14 Hz), 5.19 (1H, s), 5.47 (1H, s), 7.32-7.50 (5H, m), 7.78 (2H, d), 8.08 (1H, s), and 8.65 (2H, d); m/z (positive xenon F.A.B., thioglycerol) MH+ 711.

EXAMPLE 3

[6R,7R]-7-[[R]-2-[(4-Ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate

(a) Diphenylmethyl [6R,7R]-7-[[R]-2-[(4-Ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate Halide The title compound was prepared in a similar manner to Example 1 (a) except that 1-(pyrrolidin-1-yl)-4-thiopyridone in dichloromethane replaced 1-(3,4-dihydroxybenzoylamino)-4-thiopyridone in N,N-dimethylformamide. The product was used directly in the subsequent reaction without purification.

(b) [6R,7R]-7-[[R]-2-[(4-Ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate The title compound was prepared from diphenylmethyl [6R,7R]-7-[[R]-2-[(4-ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate halide by a similar procedure to that described in Example 1 (b) (72%); $\nu_{max}$ (KBr) 1775, 1710, and 1678 cm$^{-1}$; $\delta_H$ (D$_2$O) 1.13 (3H, t, J 7 Hz), 2.00 (4H, m), 2.94 and 3.33 (2H, ABq, J 17 Hz), 3.37 (4H, m), 3.44 (2H, q, J 7 Hz), 3.61 (2H, m), 3.92 (2H, m), 4.01 and 4.30 (2H, ABq, J 14 Hz), 5.17 (1H, s), 5.45 (1H, s), 7.2-7.5 (5H, m), 7.74 (2H, d, J 7 Hz), 8.07 (1H, s), and 8.60 (2H, d, J 7 Hz); m/z (positive xenon F.A.B., thioglycerol) MH+ 737.

EXAMPLE 4

[6R,7R]-3-[1-(N-Benzyl-N-methylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate

(a) Diphenylmethyl [6R,7R]-3-[1-(N-Benzyl-N-methylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Halide The title compound was prepared in a similar manner to Example 1 except that 1-(N-Benzyl-N-methylamino)-4-thiopyridone in dichloromethane replaced 1-(3,4-dihydroxybenzoylamino)-4-thiopyridone in N,N-dimethylformamide (70%); $\delta_H$ (CDCl$_3$+CD$_3$OD) 1.22 (3H, t, J 7 Hz), 2.90 and 2.99 (2H, ABq, J 16.5 Hz), 3.18 (3H, s), 3.57 (2H, q, J 7 Hz), 4.03 (2H, m), 4.25-4.60 (2H, m), 4.39 (2H, s), 5.24 and 5.35 (2H, ABq, J 12 Hz), 5.32 (1H, s), 5.53 (1H, s), 6.90 (1H, s), 7.15-7.57 (20H, m), 7.65 (2H, d, J 6 Hz), 8.22 (1H, s), and 8.66 (2H, d, J 6 Hz); m/z (positive xenon F.A.B., thioglycerol) M+ 953.

[6R,7R]-3-[1-(N-Benzyl-N-methylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate The title compound was prepared from diphenylmethyl [6R,7R]-3-[1-(N-benzyl-N-methylamino)-pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate halide by a similar procedure to Example 1 (50%); $\nu_{max}$ (KBr) 1787, 1715, 1684, and 1630 cm$^{-1}$; $\delta_H$ (D$_2$O) 1.13 (3H, t, J 7 Hz), 2.87 and 3.12 (2H, ABq, J 17 Hz), 3.12 (3H, s), 3.44 (2H, q, J 7 Hz), 3.58 (2H, m), 3.89 (2H, m), 4.03 and 4.22 (2H, ABq, J 14.5 Hz), 4.28 (2H, m), 5.10 (1H, s), 5.47 (1H, s), 7.07-7.53 (10H, m), 7.66 (2H, d, J 7 Hz), 8.10 (1H, s), and 8.47 (2H, d, J 7 Hz); m/z (positive xenon F.A.B., thioglycerol) MH+ 787.

EXAMPLE 5

[6R,7R]-3-[1-(N-Carbamoylmethyl-N-methylamino)-pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate

(a) Diphenylmethyl [6R,7R]-3-[1-(N-Carbamoylmethyl-N-methylamino)-pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Halide The title compound was prepared in a similar manner to Example 1 except that 1-(N-carbamoylmethyl-N-methylamino-4-thiopyridone replaced 1-(3,4-dihydroxybenzoylamino)-4-thiopyridone (50%); $\nu_{max}$ (KBr) 1785, 1710, 1677, and 1611 cm$^{-1}$; $\delta_H$ [(CD$_3$)$_2$CO] 1.19 (3H, t, J 7 Hz), 3.03 (H$_2$O covering 5H), 3.54 (2H, q, J 7 Hz), 3.74 (2H, m), 3.95–4.20 (4H, m), 4.86 (2H, m), 5.33 and 5.46 (2H, ABq, J 13.5 Hz), 5.36 (1H, s), 5.81 (1H, d, J 7 Hz), 6.94 (1H, s), 7.36–7.75 (15H, m), 8.00 (2H, d, J 7 Hz), 8.21 (1H, d, J 1 Hz), 8.95 (2H, d J 7 Hz), 9.16 (1H, s), 9.42 (1H, s), and 9.98 (1H, d, J 7 Hz); m/z (positive xenon F.A.B., thiodiethylene glycol) M+ 920.

(b) [6R,7R]-3-[1-(N-Carbamoylmethyl-N-methylamino)-pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate The title compound was prepared from diphenylmethyl [6R,7R]-3-[1-(N-carbamoyl-N-methylamino)-pyridinium-4-thiomethyl]-7-[[R]-2-[(4-ethyl-2,3-dioxopiperazin-1-yl)carbonylamino] -2-phenylacetamido]-7-formamidoceph-3-em-4-carboxylate halide in a similar procedure to Example 1 (91%); $\nu_{max}$ (KBr) 1775, 1710 sh, 1676, and 1612 cm$^{-1}$. $\delta_H$ [D$_2$O+(CD$_3$)$_2$CO] 1.14 (3H, t, J 7 Hz), 2.94 and 3.35 (2H, ABq, J 17 Hz), 3.07 (3H, s), 3.46 (2H, q, J 7 Hz), 3.65 (2H, m), 3.96 (2H, m), 4.01 (2H, s), 4.06 and 4.35 (2H, ABq, J 14 Hz), 5.19 (1H, s), 5.46 (1H, s), 7.33–7.52 (5H, m), 7.83 (2H, d, J 7 Hz), 8.08 (1H, s), and 8.72 (2H, d, J 7 Hz); m/z (positive xenon F.A.B., thioglycerol) MH+ 754.

EXAMPLE 6

[6R,7R]-7-[[R]-2-[(4-Ethyl-2,3-dioxopiperazin-1-yl)-carbonylamino]-2-phenylacetamido]-7-formamido-3-[1-[N-(3,4-dihydroxybenzoyl)-N-methylamino]pyridinium-4-thiomethyl]ceph-3-em-4-carboxylate

(a) Diphenylmethyl [6R,7R]-7-[[R]-2-[(4-Ethyl-2,3-dioxopiperazin-1-yl)carbonylamino]-2-phenylacetamido]-7-formamido-3-[1-[N-[3,4-bis(4-methoxybenzyloxy) benzoyl]-N-methylamino]pyridinium-4-thiomethyl]-ceph-3-em-4-carboxylate Halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.233 g, 0.29 mol) in dichloromethane (5 ml) was treated with 1-[N-[3,4-bis(4-methoxybenzyloxy)benzoyl]N-methylamino]4-thiopyridone (0.15 g, 0.31 mmol) for 2 hours at room temperature. Evaporation of the solvent at reduced pressure followed by chromatography on silica gel eluting with ethyl acetate, ethanol mixtures, gave the title compound (0.105 g, 31%).

(b) [6R,7R]-7-[[R]-2-[(4-Ethyl-2,3-dioxopiperazin-1-yl)carbonylamino]-2-phenylacetamido]-7-formamido-3-[1-[N-(3,4-dihydroxybenzoyl)-N-methylamino]pyridinium-4-thiomethyl]ceph-3-em-4-carboxylate Diphenylmethyl [6R,7R]-7-[[R]-2-[(4-ethyl-2,3--dioxopiperazin-1-yl)carbonylamino]-2-phenylacetamido]-7-formamido-3-[1-[N-[3,4-bis(4-methoxybenzyloxy)benzoyl]-N-methylamino]pyridinium-4-thiomethyl]ceph-3-em-4carboxylate halide (0.105 g) in dichloromethane (10 ml) was treated with trifluoroacetic acid (0.6 ml) at room temperature for 1 hour. After evaporation of solvent and excess reagent the residue was dissolved in water at pH 7.0 with sodium bicarbonate and the product purified by chromatography on Diaion HP 20SS resin eluting with mixtures of water and tetrahydrofuran. Fractions containing product were combined, reduced and freeze dried to give the title compound (0.031 g, 38%); $\nu_{max}$ (KBr) 1777, 1710 (sh), 1677, 1615, and 1512 cm$^{-1}$; $\delta_H$[D$_2$O+(CD$_3$)$_2$CO] 1.14 (3H, t, J 7 Hz), 2.97 and 3.33 (2H, ABq, J 17 Hz), 3.46 (2H, m), 3.64 (2H, m), 3.69 (3H, s), 3.95 (2H, m), 4.15 and 4.35 (2H, ABq, J 14 Hz), 5.20 (2H, s), 5.46 (1H, s), 6.80–7.55 (8H, complex), 7.94 (2H, d, J 7 Hz), 8.09 (1H, s), and 8.70 (2H, d, J 7 Hz); m/z (positive xenon F.A.B., thioglycerol/acetic acid) MH+ 833.

EXAMPLE 7

[6R,7R]-7-[[R]2-[(4-Ethyl-2,3-Dioxopiperazin-1-yl)-carbonylamino]-2-phenylacetamido]-7-formamido-3-[1-[N-(3,4-dihydroxycinnamoyl)-N-methylamino]pyridinium-4-thiomethyl]ceph-3-em-4-carboxylate

(a) Diphenylmethyl [6R,7R]-7-[[R]-2-[(4-Ethyl-2,3-dioxopiperazin-1-yl)carbonylamino]-2-phenylacetamido]-7-formamido-3-[1-[N-[3,4-bis(4-methoxybenzyloxy)cinnamoyl]-N-methylamino]pyridinium-4-thiomethyl]ceph-3-em-4-carboxylate Halide The title compound was prepared in a similar manner to Example 6 except that 1-[N-[3,4-bis(4-methoxybenzyloxy)cinnamoyl]-N-methylamino]-4-thiopyridone replaced 1-[N-[3,4-bis(4-methoxybenzyloxy)benzoyl]-N-methylamino]-4-thiopyridone (10%). This was used directly in the next stage.

(b) [6R,7R]-7-[[R]-2-[(4-Ethyl-2,3-dioxopiperazin-1-yl)-carbonylamino]-2-phenylacetamido]-7-formamido-3-[1-[N-(3,4-dihydroxycinnamoyl)-N-methylamino]pyridinium-4-thiomethyl]ceph-3-em-4-carboxylate The title compound was prepared from diphenylmethyl [6R,7R]-7-[[R]-2-[(4-ethyl-2,3-dioxopiperazin-1-yl)carbonylamino]-2-phenylacetamido]-7-formamido-3-[1-[N-[3,4-bis(4-methoxybenzyloxy)cinnamoyl]-N-methylamino]pyridinium-4-thiomethyl]-ceph-3-em-4-carboxylate halide by a similar procedure to that described in Example 6 (16%); $\delta_H$[D$_2$O+(CD$_3$)$_2$CO] 1.20 (3H, t, J 7 Hz), 3.4–4.1 (HOD covering m), 4.45 and 4.60 (2H, ABq, J 14 Hz), 5.23 (1H, s), 5.62 (1H, s), 6.85–7.70 (10H, complex), 8.16 (1H, s), 8.32 (2H, d, J 7 Hz), and 8.90 (2H, d, J 7 Hz); m/z (positive xenon F.A.B., thioglycerol) MH+ 859.

EXAMPLE 8

[6R,7R]-7-[[R]-2-[(4-Ethyl-2,3-dioxopiperazin-1-yl)carbonylamino]-2-phenylacetamido]-7-formamido-3-[1-methylamino)pyridinium-4-thiomethyl]ceph-3-em-4-carboxylate (i)

a) Diphenylmethyl [6R,7R]-7-[[R]-2-[(4-Ethyl-2,3-dioxopiperazin-1-yl)carbonylamino]-2-phenylacetamido]-7-formamido-3-[1-(methylamino)pyridinium-4-thiomethyl]-ceph-3-em-4-carboxylate Halide Diphenylmethyl [6R,7R]-7-[[R]-2-[(4-ethyl-2,3-dioxopiperazin-1-yl)carbonylamino]-2- phenylacetamido]-7-formamido-3-(halomethyl)ceph-3-em-4-carboxylate (0.8 g, 1.0 mol) in dichloromethane (20 ml) was treated with 1-(methylamino)-4-thiopyridone(0.14 g, 1.0 mol) for 2 hours at room temperature. Chromatography on silica gel eluting with mixtures of ethanol in dichloromethane gave the title compound (0.47 g, 50%)

b) [6R,7R]-7-[[R]-2-[(4-Ethyl-2,3-dioxopiperazin-1-yl)carbonylamino]-2-phenylacetamido]-7-formamido-3-[1-methylamino)pyridinium-4-thiomethyl]ceph-3-em-4-carboxylate Diphenylmethyl [6R,7R]-7-[[R]-2-[(4-ethyl-2,3-dioxopiperazin-1-yl)carbonylamino]-2-phenylacetamido]-7-formamido-3-[1-(methylamino)pyridinium-4-thiomethyl]ceph-3-em-4-carboxylate halide (0.47 g, 0.5 mol) in dichloromethane (30 ml) was treated with trifluoroacetic acid (1.25 ml) and stirred for 90 minutes. The mixture was evaporated to dryness and the residue washed with ether (3×40 ml). The product was dissolved in water at pH 7.0 with sodium bicarbonate and the product purified by chromatography on Diaion HP20ss resin eluting with mixtures of water and tetrahydrofuran.

Fractions containing product were combined and freeze dried to give the title compound (0.14 g, 41%); $\upsilon_{max}$ (KBr) 1775,1705 1676, and 1617 cm$^{-1}$; $\delta$H[D$_2$O and (CD$_3$)$_2$CO] 1.16 (3H,t,J 7 Hz), 3.02 (3H,s), 3.00 and 3.38 (2H, ABq, J 17 Hz), 3.5 (2H,q,J 7 Hz), 3.67 (2H, m) 3.98 (2H, m), 4.06 and 4.14 (2H,ABq, J 14 Hz), 5.22 (1H,s) 5.48 (1H, s) 7.36–7.8 (5H, m), 7.79 and 8.51 (4H, ABq, J 7 Hz), and 8.10 (1H,s); m/z [positive xenon F.A.B., thioglycerol/acetic acid] M+ 696.

(ii)

a) Diphenylmethyl-[6R,7R]-7-[[R]-2-[(4-Ethyl-2,3-dioxopiperazin-1-yl)carbonylamino]-2-phenylacetamido]-7-formamido-3-[1-(N-t-butyloxycarbonyl-N-methylamino)pyridinium-4-thiomethyl]ceph-3-em-4-carboxylate Halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.22 g, 27 mol)in dichloromethane (5 ml) was treated with 1-(N-t-butyloxycarbonyl-N-methylamino)-4-thiopyridone overnight. Chromatography on silica gel eluting with mixtures of ethanol in dichloromethane gave the title compound (0.195 g, 89%) $\delta_H$(CDCl$_3$) 1.2 (3H, t, J 7 Hz), 1.48 (9H, s), 3.37 and 3.48 (2H, ABq, J 16 Hz), 3.54 (2H, q, J 7 Hz), 3.66 (3H, s), 3.7 (2H, m), 4.62 and 4.74 (2H, ABq, J 13 Hz), 5.36 (1H, d, J 7 Hz), 6.98 (1H, s),7.2–7.7 (15H, m), 8.14 and 9.09 (4H, ABq, J 7 Hz),8.30 (1H,s), and 10.0 (1H, d, J 7 Hz); m/z [positive xenon F.A.B., 3-nitrobenzylalcohol] M+ 693.

b) [6R, 7R]-7-[[R]-2-[(4-Ethyl-2,3-dioxopiperazin-1-yl)carbonylamino]-2-phenylacetamido]-7-formamido-3-[1-(methylamino)pyridinium-4-thiomethyl]ceph-3-em-4-carboxylate Diphenylmethyl [6R,7R]-7-[[R]-2-[(4-ethyl-2,3-dioxopiperazin-1-yl)carbonylamino]-2-phenylacetamido]-7-formamido-3-[1-(N-t-butyloxycarbonyl-N-methylamino) pyridinium-4-thiomethyl]ceph-3-em-4-carboxylate halide (0.18 g, 0.17 mol) was treated with trifluoroacetic acid (3 ml) for 30 minutes and evaporated to dryness. The residue was washed with ether(2×40 ml) and the product dissolved in water with sodium bicarbonate to pH7 then purified by chromatography on Diaion HP20SS eluting with mixtures of tetrahydrofuran and water. Fractions containing product were combined and freeze dried to give the title compound (0.024 g, 20%) which was identical by i.r, n.m.r, m.s to that prepared in Example 8 (i) above.

EXAMPLE 9

[6R,7R]-7-[[R]-2-[(4-Ethyl-2,3-dioxopiperazin-1-yl)carbonylamino]-2-phenylacetamido]-7-formamido-3-[1-(N-acetyl-N-methylamino)pyridinium-4-thiomethyl]ceph-3-em-4-carboxylate a) Diphenylmethyl [6R,7R]-7-[[R]-2-[(4-Ethyl-2,3-dioxopiperazin-1-yl) carbonylamino]-2-phenylacetamido]-7-formamido-3-[1-(N-acetyl-N-methylamino)pyridinium-4-thiomethyl]-ceph-3-em-4-carboxylate Halide Diphenylmethyl [6R,7R]-7-[[R]-2-[(4-ethyl-2,3-dioxopiperazin-1-yl)carbonylamino]-2- phenylacetamido]-7-formamido-3-(halomethyl)ceph-3-em-4-carboxylate (0.2 g, 0.25 mol) in dichloromethane (10 ml) was treated with 1-(N-acetyl-N-methylamino)-4-thiopyridone(0.045 g, 0.25 mol) for 2 hours at room temperature. The mixture was evaporated to dryness and the residue washed with ethyl acetate (2×10 ml) to give the title product (0.18 g, 73%) which was deprotected without further purification.

b) [6R, 7R]-7-[[R]-2-[(4-Ethyl-2,3-dioxopiperazin-1-yl)carbonylamino]-2-phenylacetamido]-7-formamido-3-[1-(N-acetyl-N-methylamino)pyridinium-4-thiomethyl]ceph-3-em-4-carboxylate Diphenylmethyl [6R, 7R]-7-[[R]-2-[(4-ethyl-2,3-dioxopiperazin-1-yl) carbonylamino]-2-phenylacetamido]-7-formamido-3-[1-(N-acetyl-N-methylamino)pyridinium-4-thiomethyl]ceph-3-em-4-carboxylate halide (0.18 g, 0.18 mmol) in dichloromethane (20 ml) was treated with trifluoroacetic acid (1.5 ml) for 1 hour. The mixture was evaporated to dryness and washed with ether (2×20 ml). The product was dissolved in water with sodium bicarbonate to pH 7 and purified by chromatography on Diaion HP20SS eluting with mixtures of tetrahydrofuran and water. Fractions containing product were combined and freeze dried to give the title compound (0.1 g, 76%); $\upsilon_{max}$ (KBr) 1775, 1710, 1684, and 1616 cm$^{-1}$; $\delta$H(D$_2$O) 1.14 (3H, t, J 7 Hz), 2.33 (3H, s), 2,95 and 3.36 (2H, ABq, J 17 Hz), 3.46 (2H, q, J 7 Hz), 3.6–3.7 (2H, m), 3.7 (3H,s), 3.9–4 (2H, m), 4.13 and 4.40 (2H, ABq, J 14 Hz), 5.21 (1H, s), 5.46 (1H, s), 7.3–7.5 (5H, m), 7.70

(2H, d, J 7 Hz), 8.08 (1H, s), and 8.50 (2H,d, J 7 Hz); m/z (positive xenon F.A.B., thioglycerol) M+ 739.

EXAMPLE 10

[6R,7R]-7-[[R]-2-[(4-Ethyl-2,3-dioxopiperazin-1-yl)-carbonylamino]-2-phenylacetamido]-7-formamido-3-[1-(N-formyl-N-methylamino)pyridinium-4-thiomethyl]-ceph-3-em-4-carboxylate a)

Diphenylmethyl[6R,7R]-7-[[R]-2-[(4-Ethyl-2,3-dioxopiperazin-1-yl)carbonylamino]-2-phenylacetamido]-7-formamido-3-[1-(N-formyl-N-methylamino)pyridinium-4-thiomethyl]ceph-3-em-4-carboxylate Halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.2 g, 0.25 mol) in dichloromethane (10 ml) was treated with 1-(N-formyl-N-methylamino)-4-thiopyridone (0.043 g, 0 26 mol) for 2 hours at room temperature, during which time the product precipitated from solution. The solid was collected and washed with dichloromethane(5 ml) to give the title compound (0.11 g, 45%) which was deprotected without further purification.

b) [6R,7R]-7-[[R]-2-[(4-Ethyl-2,3-dioxopiperazin-1-yl)-carbonylamino]-2-phenylacetamido]-7-formamido-3-[1-(N-formyl-N-methylamino)pyridinium-4-thiomethyl]ceph-3-em-4-carboxylate Diphenylmethyl [6R,7R]-7-[[R]-2-[(4-ethyl-2,3-dioxopiperazin-1-yl)carbonylamino]-2-phenylacetamido]-7-formamido-3-[1-(N-formyl-N-methylamino)pyridinium-4-thiomethyl]ceph-3-em-4-carboxylate halide (0.11 g) was treated with trifluoroacetic acid for 15 minutes at room temperature. The mixture was evaporated to dryness and washed with ether(2×15 ml). The product was dissolved in water with sodium bicarbonate to pH7 and purified by chromatography on Diaion HP20SS eluting with mixtures of tetrahydrofuran and water. Fractions containing product were combined and freeze dried to give the title compound (0.047 g,26%) ; $\nu_{max}$ (KBr) 1775, 1700, 1684, and 1616 cm$^{-1}$ $\delta$H(D$_2$O ) 1.14 (3H, t, J 7 Hz), 3.45 (2H, q, J 7 Hz), 3.6-3.7 (3H, s+2H, m), 3.9-4.0 (2H, m) 4.13 and 4.33 (2H, ABq, J 14 Hz), 5.21 (1H,s), 5.45 (1H, s), 7.3-7.5 (5H, m), 7.95 (2H, d, J 7 Hz), 8.08 (1H,s), 8.37 (1H, s), and 8.52 (2H, d, J 7 Hz); m/z (positive xenon F.A.B., thioglycerol) MH+ 725.

EXAMPLE 11

[6R,7R]-7-[[R]-2-[(4-Ethyl-2,3-dioxopiperazin-1-yl)carbonylamino]-2-phenylacetamido]-7-formamido-3-[1-[N-methyl-N-(4-nitrobenzoyl)amino]pyridinium-4-thiomethyl]ceph-3-em-4-carboxylate a) Diphenylmethyl [6R,7R]-7-[[R]-2-[(4-Ethyl-2,3-dioxopiperazine-1--yl)carbonylamino]-2-phenylacetamido]-7-formamido-3-[1-[1-[N-(4-nitrobenzoyl)-N-methylamino]-pyridinium-4-thiomethyl]ceph-3-em-4-carboxylate Halide Diphenylmethyl [6R,7R]-7-[[R]-2-[(4-ethyl-2,3-dioxopiperazin-1-yl)carbonylamino]-2-phenylacetamido]-7-formamido-3-halomethylceph-3-em-4-carboxylate (200 mg, 0.26 mol) in acetonitrile (15 ml) was treated with 1-[N-(4-nitrobenzoyl)-N-methylamino]-4-thiopyridone (79 mg, 0.27 mol) for 2½ h. The product was then isolated by silica gel chromatography eluting with mixtures of methanol, dichloromethane to give the title compound (140 mg, 51%); $\delta_H$ [(CD$_3$)$_2$CO] 1.14 (3H, t, J 7 Hz), 3.30 and 3.44 (2H, ABq, J 15 Hz), overlaying 3.47 (2H, q, J 7 Hz), 3.66 (2H, m), 3.74 (3H, s), 3.99 (2H, m), 5.32 (1H, s), 5.56 (1H, s), 6.88 (1H, s), 7.1-7.5 (15H, m), 7.90 (2H, d, J 7 Hz), 8.00 (2H, d, J 8 Hz), 8.19 (1H, s), 8.35 (2H, d, J 8 Hz), and 8.91 (2H, d, J 7 Hz).

b) [6R,7R]-7-[[R]-2-[(4-Ethyl-2,3-dioxopiperazin-1-yl)carbonylamino]-2-phenylacetamido]-7-formamido-3-[1-[N-methyl-N-(4-nitrobenzoyl)amino]pyridinium-4-thiomethyl]ceph-3-em-4-carboxylate The product of Example 11(a) (87 mg) was dissolved in 10% trifluoroacetic acid in dichloromethane (5 ml, excess) for 30mins. The mixture was evaporated under reduced pressure and the residue was extracted with water neutralising to pH 7 with sodium bicarbonate. The aqueous extracts were chromatographed on Diaion HP20SS resin eluting with mixtures of water and tetrahydrofuran. Fractions containing product were combined and freeze-dried to give the title compound (27 mg, 40%); $\nu_{max}$(KBr) 1775, 1710, 1684, and 1617 cm$^{-1}$; $\delta_H$[D$_2$O+(CD$_3$)$_2$CO] 1.22 (3H, t, J 7 Hz), 3.14 and 3.49 (2H, ABq, J 17 Hz), partially overlaying 3.56 (2H, q, J 7 Hz), 3.76 (2H, m), 3.83 (3H, s), 4.07 (2H, m), 5.28 (1H, s), 5.64 (1H, s), 7.40 (3H, m), 7.57 (2H, m), 8.10 (1H, s), 8.19 (2H, d, J 7 Hz), 8.27 (2H, d, J 7 Hz), 8.44 (2H, d, J 7 Hz), and 9.04 (2H, d, J 7 Hz); m/z (positive xenon F.A.B., thioglycerol) MH+ 846.

EXAMPLE 12

[6R,7R]-7-[[R]-2-[(4-Ethyl-2,3-dioxopiperazin-1-yl)carbonylamino]-2-phenylacetamido]-2-phenylacetamido]-7-formamido-3-[1-[N-methyl-N-(4-methoxybenzoyl)amino]pyridinium-4-thiomethyl]ceph-3-em-4-carboxylate a) Diphenylmethyl [6R,7R]-7-[[R]-2-[(4-Ethyl-2,3-dioxopiperazin-1-yl)carbonylamino]-2-phenylacetamido]-7-formamido-3-[1-N-(4-methoxybenzoyl)-N-methylamino]pyridinium-4-thiomethyl]ceph-3-em-4-carboxylate Halide The product of Description 2 (108 mg, 0.14 mol) in acetonitrile (10 ml) was treated with 1[N-(4-methoxybenzoyl)-N-methylamino]-4-thiopyridone (37 mg, 0.14 mol) for 2 h. The product was then chromatographed on silica gel eluting with mixtures of methanol and dichloromethane to give the title compound (72 mg, 50%); $\delta_H$ (CDCl$_3$+CD$_3$OD) 1.90 (3H, t, J 7 Hz), 3.4-3.6 (4H, m), 3.78 (3H, s), 3.86 (3H, s), 4.25 and 4.60 (2H, ABq, J 14 Hz), 5.34 (1H, s), 5.66 (1H, s), 6.93 (1H, s), 6.99 (2H, d, J 9 Hz), 7.2-7.6 (15H, m), 7.8 (4H, m), 8.19 (1H, 6), and 8.69 (2H, d), J 6 Hz); m/z (positive xenon F.A.B., thioglycerol); MH+ 997.

b) [6R,7R]-7-[[R]-2-[(4-Ethyl-2,3-dioxopiperazin-1-yl)carbonylamino]-2-phenylacetamido]-7-formamido-3-[1-[N-methyl-N-(4-methoxybenzoyl)amino]pyridinium-4-thiomethyl]ceph-3-em-4-carboxylate The product of Example 12(a) (64 mg) was dissolved in 5% trifluoroacetic acid in dichloromethane (10 ml) for 45 min. The mixture was then evaporated to dryness under reduced pressure and the residue was extracted with water neutralising to pH 7 with sodium bicarbonate. The aqueous extracts were chromatographed on Diaion HP20SS resin eluting with mixtures of water and tetrahydrofuran. Fractions containing the product were combined and freeze-dried to give the title compound (29 mg, 35%); $\nu_{max}$ (KBr) 1776, 1710, 1680, and 1605 cm$^{-1}$; $\delta_H$ [D$_2$O+(CD$_3$)$_2$CO] 1.37 (3H, t, J 7 Hz), 3.28 and 3.64 (2H, ABq, J 17 Hz), partially overlaying 3.71 (2H, q, J 7 Hz), 3.93 (2H, m), 3.98 (3H, s), 4.08 (3H, s), 4.22 (2H, m), 4.52 and 4.67 (2H, ABq, J 14 Hz), 5.43 (1H, s), 5.77 (1H, s), 7.27 (2H, d, J 9 Hz), 7.56 (3H, m), 7.72 (3H, m), 7.91 (2H, d, J 9 Hz), 8.34 (1H, s), overlaying 8.36 (2H, d, J 7 Hz), and 9.09 (2H, d, J 7 Hz); m/z (positive xenon F.A.B., thioglycerol) MH+ 831.

EXAMPLE 13

[6R,7R]-7-[[R]-2-[(4-Ethyl-2,3-dioxopiperazin-1-yl)carbonylamino]-2-phenylacetamido]-7-formamido-3-[1-N-methyl-N-(2-furoyl)amino]pyridinium-4-thiomethyl]-ceph-3-em-4-carboxylate a) Diphenylmethyl [6R,7R]-7-[[R]-2-[-(4-Ethyl-2,3-dioxopiperazin-1-yl)carbonylamino]-2-phenylacetamido]-7-formamido-3-[1-[N-(2-furoyl)-N-methylamino]pyridinium-4-thiomethyl]ceph-3-em-4-carboxylate Halide The product of Description 2 (100 mg, 0.13 mol) in acetonitrile (10 ml) was treated with 1-[N-(2-furoyl)-N-methylamino]-4-thiopyridone (Preparation 11) (30 mg, 0.13 mmol). After 30mins sodium iodide (30 mg, 0.21 mol) in a little acetone was added. The mixture was stirred a further 30 mins then the product was isolated by chromatography on silica gel eluting with mixtures of methanol and dichloromethane to give the title compound (84 mg, 62%); $\nu_{max}$ (KBr) 1787, 1710, 1680, and 1613 cm$^{-1}$; $\delta_H$ (CDCl$_3$+CD$_3$OD) 1.21 (3H, t, J 7 Hz), 3.54 (4H, m), 3.95 (3H, s), 4.04 (2H, m), 4.42 and 4.66 (2H, ABq, J 12 Hz), 5.31 (1H, s), 5.56 (1H, d, J 6 Hz), 6.60 (1H, dd, J 1.5, 3.5 Hz), 6.94 (1H, s), 7.18–7.56 (16H, m), 7.58 (1H, d, J 1.5 Hz), 8.50 (2H, d, J 7 Hz), and 9.87 (1H, d, J 6 Hz).

b) [6R,7R]-7-[[R]-2-[(4-Ethyl-2,3-dioxopiperazin-1-yl)carbonylamino]-2-phenylacetamido]-7-formamido-3-[1-[N-(2-furoyl)-N-methylamino]pyridinium-4-thiomethyl]-ceph-3-em-4-carboxylate The product of Example 13(a) (75 mg) was dissolved in 5% trifluoroacetic acid in dichloromethane (20 ml) for 45 mins. The mixture was then evaporated to dryness under reduced pressure and the residue was extracted with water, neutralising to pH 7.0 using sodium bicarbonate. The aqueous extracts were chromatographed on Diaion HP20SS resin, eluting with mixtures of water and tetrahydrofuran. Fractions containing the product were combined and freeze-dried to give the title compound (41 mg, 75%); $\nu_{max}$ (KBr) 1780, 1710, 1680, and 1615 cm$^{-1}$; $\delta_H$[D$_2$O+(CD$_3$)CO] 1.22 (3H, t, J 7 Hz), 3.71 and 3.51 (2H, ABq, J 17 Hz), 3.76 (2H, m), 3.95 (3H, s), 4.07 (2H, m), 4.45 and 4.64 (2H, ABq, J 26 Hz) overlayed by HOD resonance, 5.27 (1H, s), 5.61 (1H, s), 6.71 (1H, dd, J 1.6 and 3.5 Hz), 7.29 (1H, d, J 3.5 Hz), 7.40 (3H, m), 7.57 (2H, m), 7.76 (1H, brs), 8.18 (1H, s), 8.28 (2H, dd, J 7 Hz), and 8.96 (2H, d, J 7 Hz).

EXAMPLE 14

[6R,7R]-3-(1-Aminopyridinium-4-thiomethyl)-7-[[R]-2-[(4-ethyl-2,3-dioxopiperazin-1-yl)carbonylamino]-2-phenylacetamido]-7-formamidoceph-3-em-4-carboxylate a) Diphenylmethyl [6R,7R]-3-[1-(t-Butyloxycarbonylamino)pyridinium-4-thiomethyl]-7-[[R-2-(4-ethyl-2,3-dioxopiperazin-1-yl)carbonylamino]-2-phenylacetamido]-7-formamidoceph-3-em-4-carboxylate Halide The title compound was prepared in a similar manner to Example 1 except that 1-(t-butyloxycarbonylamino)-4-thiopyridone in dichloromethane replaced 1-(3,4-dihydroxybenzoylamino)-4-thiopyridone in N,N-dimethylformamide (42%); M+ 949.

b) [6R,7R]-3-(1-Aminopyridinium-4-thiomethyl)-7-[[R]-2-[(4-ethyl-2,3-dioxopiperazin-1-yl)carbonylamino]-2-phenylacetamido]-7-formamidoceph-3-em-4-carboxylate The title compound was prepared from the product of Example 14(a) by a similar procedure to Example 1(b) (53%); $\nu_{max}$ (KBr) 1775, 1710, 1677, and 1611 cm$^{-1}$; $\delta_H$ (D$_2$O) 1.19 (3H, t, J 7 Hz), 3.03 and 3.41 (2H, ABq, J 17 Hz), 3.52 (2H, q, J 7 Hz), 3.71 (2H, m), 4.03 (2H, m), 4.12 and 4.36 (2H, ABq, J 14 Hz), 5.24 (1H, s), 5.52 (1H, s), 7.45 (5H, m), 7.79 (2H, d, J 7 Hz), 8.14 (1H, s), and 8.43 (2H, d); m/z (positive xenon F.A.B., thioglycerol) MH+ 683.

EXAMPLE 15

[6R,7R]-3-[1-(Carboxymethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate a) Diphenylmethyl [6R,7R]-3-[1-[N-(t-Butyloxycarbonyl)-N-(t-butyloxycarbonylmethyl)amino]pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Iodide The product from Description 2 (0.10 g, 0.13 mol) in acetone (5 ml) was treated with sodium iodide (0.02 g, 0.13 mol) and stirred for 0.75 h. The precipitate was removed by filtration and the filtrate evaporated under reduced pressure. The iodide was dissolved in dichloromethane (10 ml) and treated with 1-[N-(t-butyloxycarbonyl)-N-(t-butyloxycarbonylmethyl)amino]-4-thiopyridone (0.088 g, 0.26 mol). The mixture was stirred for 2 h, then chromatographed on silica gel 60, eluting with ethanol, dichloromethane mixtures (0.085 g, 60%); $\nu_{max}$ (KBr) 1789, 1715, 1685, and 1616 cm$^{-1}$; $\delta_H$ (CDCl$_3$+CD$_3$OD) 1.22 (3H, t, J 7 Hz), 1.51 (18H, s), 3.20 (2H, m), 3.54 (4H, m), 4.03 (2H, m), 4.33 (2H, m), 4.60 (2H, m), 5.30 (1H, s), 5.52 (1H, d, J 6 Hz), 6.93 (1H, s), 7.20–7.55 (15H, m), 7.73 (3H, m), 8.21 (1H, s), 8.70 (2H, d, J 7 Hz), 9.91 (1H, d, J 6 Hz); m/z (positive xenon F.A.B., thioglycerol) M+ 1063.

b)

[6R,7R]-3-[1-(Carboxymethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate The product from Example 15(a) (0.075 g, 0.064 mol) was treated with trifluoroacetic acid (1 ml) and stirred for 30mins. The mixture was evaporated under reduced pressure and the residue diluted with toluene (1 ml), dichloromethane (1 ml) and evaporated to dryness. Purification on Diaion HP20SS resin eluting with acetone, water mixtures afforded the title compound (0.025 g, 52%); $\nu_{max}$ (KBr) 1778, 1713, 1677, and 1618 cm$^{-1}$; $\delta_H$(D$_2$O) 1.14 (3H, t, J 7 Hz), 2.92–3.33 (2H, ABq, J 17 Hz), 3.47 (2H, q, J 7 Hz), 3.65 (2H, m), 4.00 (2H, m), 4.04 (2H, s), 4.06–4.32 (2H, ABq, J 14 Hz), 5.20 (1H, s), 5.46 (1H, s), 7.40 (5H, m), 7.74 (2H, d, J 7 Hz), 8.09 (1H, s), and 8.55 (2H, d, J 7 Hz); m/z (positive xenon F.A.B., thioglycerol) MH+ 741.

EXAMPLE 16

[6R,7R]-3-[1-(Diphenylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate a) Diphenylmethyl [6R,7R]-3-[1-(Diphenylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate Halide The product from Description 2 (0.04 g, 0.05 mole) in dichloromethane (5 ml) was treated with 1-(diphenylamino)-4-thiopyridone (0.02 g, 0.072 mole). The mixture was stirred for 18 h, then evaporated under reduced pressure to give the title compound which was used in the next stage without purification.

b)

[6R,7R]-3-[1-(Diphenylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate The crude product from Example 16(a) was treated with trifluoroacetic acid (1 ml) and stirred for 10 min. The mixture was evaporated under reduced pressure and the residue diluted with toluene and evaporated three times to dryness. Purification on Diaion HP20SS resin eluting with acetone, water mixtures afforded the title compound (0.013 g, 31%); $\nu_{max}$ (KBr) 1778, 1715, 1680, and 1615 cm$^{-1}$; $\delta_H$(D$_2$O) 1.18 (3H, t, J 7.2 Hz), 2.74 and 3.42 (2H, ABq, J 17 Hz), 3.50 (2H, 2d, J 7.2 Hz), 3.60–3.80 (2H, m), 3.90–4.10 (2H, m), 4.27 and 4.40 (2H, ABq, J 13 Hz), 5.21 (1H, s), 5.50 (1H, s), 7.00–7.15 (5H, m), 7.25–7.55 (10H, m), 8.07 and 8.88 (4H, 2d, J 7 Hz), and 8.12 (1H, s); m/z (positive xenon F.A.B., thioglycerol) MH+ 835.

EXAMPLE 17

[6R,7R]-7-[R]-2-[(4-Ethyl-2,3-dioxopiperazin-1yl)carbonylamino]-2-phenylacetamido]-3-[1-[N-(2-hydroxyethyl)-N-methylamino]pyridinium-4-thiomethyl]-7-formamidoceph-3-em-4-carboxylate a) Diphenylmethyl [6R,7R]-7-[[R]-2-[(4-ethyl-2,3-dioxopiperazin-1-yl)carbonylaminol-2-phenylacetamido]-3-[N-(2-hydroxyethyl)-N-methylamino]pyridinium-4thiomethyl]-7-formamidoceph-3-em-4-carboxylate Halide The product from Description 2 (0.1 g, 0.125 mole) in dichloromethane (5 ml) was treated with 1-[N-(2-hydroxyethyl)-N-methylamino]-4-thiopyridone (0.034 g, 0.185 mole). The mixture was stirred for 3.5 h, then evaporated under reduced pressure to give the title compound which was used in the next stage without purification.

b)

[6R,7R]-7-[[R]-2-[(4-Ethyl-2,3-dioxopiperazin-1-yl)-carbonylamino]-2-phenylacetamido]-3-[1-[N-(2-hydroxyethyl)-N-methylamino]pyridinium-4-thiomethyl]-7-formamidoceph-3-em-4-carboxylate The crude product from Example 17(a) was treated with trifluoroacetic acid (1 ml) and stirred for 10 min. The mixture was evaporated under reduced pressure and the residue diluted with toluene and evaporated to dryness three times. Purification on Diaion HP20SS resin eluting with acetone, water mixtures afforded the title compound (0.071 g, 77%); $\nu_{max}$ (KBr) 1778, 1710, 1680, and 1615 cm$^{-1}$; $\delta_H$(D$_2$O ) 1.17 (3H, t, J 7.2 Hz), 2.97 and 3.37 (2H, ABq, J 17.2 Hz), 3.05 (3H, s), 3.34 (2H, m), 3.50 (2H, q, J 7.2 Hz), 3.52–3.73 (4H, m), 3.90–4.14 (2H, m), 4.07 and 4.38 (2H, ABq, J 7.2 Hz), 5.20 (1H, s), 5.49 (1H, s), 7.36–7.50 (5H, m), 7.61 and 8.69 (4H, 2d), and 8.1 (1H, s); m/z (positive xenon F.A.B., thioglycerol) MH+ 741.

EXAMPLE 18

[6R,7R]-7-[[R]-2-[(4-Ethyl-2,3-dioxopiperazin-1-yl)carbonylamino]-2-phenylacetamido]-3-[1-(hexahydro-1H-azepin-1-yl)pyridinium-4-thiomethyl]-7-formamidoceph-3-em-4-carboxylate a) Diphenylmethyl [6R,7R]-7-[[R]-2-(4-Ethyl-2,3-dioxopiperazin-1-yl)carbonylamino]-2-phenylacetamido]-3-[1-(hexahydro-1H-azepin-1-yl)pyridinium-4-thiomethyl]-7-formamidoceph-3-em-4-carboxylate Halide The product from Description 2 (0.1 g, 0.125 mole) in dichloromethane (5 ml) was treated with 1-(hexahydro-1H-azepin-1-yl)-4-thiopyridone (0.05 g, 0.25 mole). The mixture was stirred for 6.0 h, then evaporated under reduced pressure to give the title compound, which was used in the next stage without purification.

b)

[6R,7R]-7-[[R]-2-[(4-Ethyl-2,3-dioxopiperazin-1-yl)carbonylamino]-2-phenylacetamido]-3-[1-(hexahydro-1H-azepin-1-yl)pyridinium-4-thiomethyl]-7-formamidoceph-3-em-4-carboxylate The crude product from Example 18(a) was treated with trifluoroacetic acid (1 ml) and stirred for 10 mins. The mixture was evaporated under reduced pressure and the residue diluted with toluene and evaporated to dryness three times. Purification or Diaion HP20SS resin eluting with acetone, water mixtures afforded the title compound (0.06 g, 63%); $v_{max}$ (KBr) 1778, 1715, 1685 and 1615 cm$^{-1}$; $\delta_H$ (D$_2$O) 1.14 (3H, t, J 7.2 Hz), 1.66 (4H, s), 1.80 (4H, s), 2.98–3.39 (2H, ABq, J 17 Hz), 3.37 (4H, s), 3.48 (2H, q, J 7.2 Hz), 3.61–3.70 (2H, m), 3.90–4.04 (2H, m), 4.05 and 4.33 (2H, ABq, J 13 Hz), 5.20 (1H, s), 5.47 (1H, s), 7.30–7.60 (5H, m), 7.79 and 8.65 (4H, 2d, J 7 Hz), and 8.1 (1H, s); m/z (positive xenon F.A.B., thioglycerol) MH+ 765.

EXAMPLE 19

[6R,7R]-7-[[R]-2-[(4-Ethyl-2,3-dioxopiperazin-1-yl)carbonylamino]-2-phenylacetamido]-3-[1-[4-(2-hydroxyethyl)piperazin-1-yl]pyridinium-4-thiomethyl]-7-formamidoceph-3-em-4-carboxylate a) Diphenylmethyl [6R,7R]-7-[[R]-2-[(4-Ethyl-2,3-dioxopiperazin-1-yl)carbonylamino]-2-phenylacetamido]-3-[1-(4-(2-hydroxyethyl)piperazin-1-yl)pyridinium-4-thiomethyl)-7-formamidoceph-3-em-4-carboxylate Iodide The product from Description 2 (0.1 g, 0.125 mmole) in acetone (5 ml) was treated with sodium iodide (0.018 g, 0.125 mmole) and stirred for 1 h. The precipitated sodium chloride was removed by filtration and the filtrate evaporated under reduced pressure. The residual solid was dissolved in chloroform (5 ml) and treated with 1-[4-(2-hydroxyethyl)piperazin-1-yl-4-thiopyridone (0.05 g, 0.3 mmole). The reaction mixture was stirred at room temperature for 18 h, then evaporated under reduced pressure to give the title compound which was used in the next stage without purification.

b) [6R,7R]-7-[[R]-2-[(4-Ethyl-2,3-dioxopiperazin-1-yl)carbonylamino]-2-phenylacetamido]-3-[1-[4-(2-hydroxyethyl)piperazin-1-yl]pyridinium-4-thiomethyl]-7-formamidoceph-3-em-4-carboxylate The crude product from Example 19(a) was treated with trifluoroacetic acid (1 ml) and stirred for 10 minutes. The mixture was evaporated under reduced pressure and the residue diluted with toluene and evaporated to dryness three times. Purification on Diaion HP20SS resin eluting with acetone, water mixtures afforded the title compound (0.028 g, 28%); $v_{max}$ (KBr) 1778, 1710, 1675, and 1615 cm$^{-1}$; $\delta_H$(D$_2$O) 1.15 (3H, t, J 7.2 Hz), 2.98 and 3.34 (2H, ABq, J 17 Hz), 3.38 (2H, s), 3.5 (2H, q, J 7.2 Hz), 3.58–3.70 (10H, m), 3.87–4.10 (4H, m), 5.40 (1H, s), 5.51 (1H, s), 7.42 (5H, m), 7.60 and 8.68 (4H, 2d, J 7 Hz), and 8.10 (1H, s); m/z (positive xenon F.A.B., thioglycerol) MH+ 796.

EXAMPLE 20

[6R,7R]-7-[[R]-2-[(4-Ethyl-2,3-dioxopiperazin-1-yl)carbonylamino]-2-phenylacetamido]-3-[1-(morpholin-4-yl)pyridinium-4-thiomethyl]-7-formamidoceph-3-em-4-carboxylate a) Diphenylmethyl [6R,7R]-7-[[R]-2-[(4-Ethyl-2,3-dioxopiperazin-1-yl)carbonylamino]-2-phenylacetamido]-3-[1-(morpholin-4-yl)pyridinium-4-thiomethyl]-7-formamidoceph-3-em-4-carboxylate Iodide The product from Description 2 (0.1 g, 0.125 mmole) in acetone (5 ml) was treated with sodium iodide (0.018 g, 0.125 mmole) and stirred for 1 h. The precipitated sodium chloride was removed by filtration and the filtrate evaporated under reduced pressure. The residual solid was dissolved in chloroform (5 ml) and treated with 1-(morpholin-4-yl)-4-thiopyridone (0.06 g, 0.3 mmole). The reaction mixture was stirred at room temperature for 18 h, then evaporated under reduced pressure to give the title compound, which was used in the next reaction stage without purification.

b) [6R,7R]-7-[[R]-2-[(4-Ethyl-2,3-dioxopiperazin-1-yl)carbonylamino]-2-phenylacetamido]-3-[1-(morpholin-4-yl)pyridinium-4-thiomethyl]-7-formamidoceph-3-em-4-carboxylate The crude product from Example 20(a) was treated with trifluoroacetic acid (2 ml) and stirred for 10 min. The mixture was evaporated under reduced pressure and the residue diluted with toluene and evaporated to dryness three times. Purification on Diaion HP20SS resin eluting with acetone, water mixtures afforded the title compound (0.072 g, 77%); $v_{max}$ (KBr) 1778, 1710, 1675, ad 1610 cm$^{-1}$; $\delta_H$ (D$_2$O) 1.14 (3H, t, J 7.2 Hz), 2.97 and 3.40 (2H, d and m), 3.30 (4H, m), 3.50 (2H, q, J 7.2 Hz), 3.59–3.68 (2H, m), 3.80–4.04 (6H, m), 4.07 and 4.31 (2H, ABq, J 13 Hz), 5.20 (1H, s), 5.48 (1H, s), 7.30–7.60 (5H, m), 7.85 and 8.68 (4H, 2d), and 8.07 (1H, s); m/z (positive xenon F.A.B., thioglycerol) MH+ 753.

EXAMPLE 21

[6R,7R]-7-[[R]-2-[(4-Ethyl-2,3-dioxopiperazin-1-yl)carbonylamino]-2-phenylacetamido]-7-formamido-3-[1-(2-oxopyrrolidin-1-yl)pyridinium-4-thiomethyl]ceph-3-em-4-carboxylate a) Diphenylmethyl [6R,7R]-7-[[R]-2-[(4-Ethyl-2,3-dioxopiperazin-1-yl)carbonylamino]-2-phenylacetamido]-7-formamido-3-[1-(2-oxopyrrolidin-1-yl)pyridinium-4-thiomethyl]ceph-3-em-4-carboxylate halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.08 g, 0.1 mmol) was dissolved in acetonitrile (5 ml) and treated sequentially with 1-(2-oxopyrrolidin-1-yl)-4-thiopyridone (0.0194 g, 0.1 mmol) and sodium iodide (0.015 g, 0.1 mmol) at room temperature. After 1 h the reaction mixture was chromatographed on silica gel 60, eluting with dichloromethane then ethyl acetate and, finally, mixtures of methanol in dichloromethane, to give the title compound (0.0893 g, 86%); $v_{max}$ (KBr) 1786, 1713, 1679 and 1616 cm$^{-1}$; $\delta_H$(CDCl$_3$+CD$_3$OD) 1.22 (3H, t, J 7 Hz), 2.36 (2H, t, J 7 Hz), 2.59 (2H, t, J 7 Hz), 3.01 and 3.11 (2H, ABq, J 16 Hz), 3.48–3.65 (4H, m), 3.97–4.09 (2H, m), 4.20 (2H, t, J 7 Hz), 4.33 and 4.48 (2H, ABq, J 13 Hz), 5.30 (1H, s), 5.53 (1H, d, J 6 Hz), 6.94 (1H, s), 7.20–7.55 (15H, m), 7.78 (1H, d, J 7 Hz), 8.19 (1H, s), 8.66 (2H, d, J 7 Hz), and 9.89 (1H, d, J 6 Hz, exch.); m/z (positive xenon F.A.B., 3-nitrobenzylalcohol) M+ 917.

b) [6R,7R]-7-[[R]-2-[(4-Ethyl-2,3-dioxopiperazin-1-yl)carbonylamino]-2-phenylacetamido]-7-formamido-3-[1-(2-oxopyrrolidin-1-yl)pyridinium-4-thiomethyl]ceph-3-em-4-carboxylate The product of Example 21(a) (0.08 g, 0.08 mmol) was treated with trifluoroacetic acid (0.262 g, 2.3 mmol) in dichloromethane (3.5 ml) as described in Example 6 and the title compound obtained after freeze-drying (0.024 g, 42%); $v_{max}$ (KBr) 1775, 1710, 1677 and 1617 cm$^{-1}$; $\delta_H$(D$_2$O) 1.21 (3H, t, J 7 Hz), 2.30–2.50 (2H, m), 2.51 (2H, t, J 8 Hz), 3.08 and 3.46 (2H, ABq, J 17 Hz), 3.54 (2H, q, J 7 Hz), 3.66–3.79 (2H, m), 3.90–4.10 (2H, m), 4.15 (2H, t, J 7 Hz), 4.28 and 4.42 (2H, ABq, J 14 Hz), 5.27 (1H, s), 5.55 (1H, s), 7.35–7.58 (5H, m), 8.08 (2H, d, J 7 Hz), 8.16 (1H, s), and 8.67 (2H, d, J 7 Hz); m/z (positive xenon F.A.B., thioglycerol/acetic acid), MH+ 751.

EXAMPLE 22

[6R,7R]-7-[[R]-2-[(4-Ethyl-2,3-dioxopiperazin-1-yl)carbonylamino]-2-phenylacetamido]-7-formamido-3-[1-(2-oxopiperidin-1-yl)pyridinium-4-thiomethyl]ceph-3-em-4-carboxylate a) Diphenylmethyl [6R,7R1-7-[[R]-2-[(4-Ethyl-2,3-dioxopiperazin-1-yl)carbonylamino]-2-phenylacetamido]-7-formamido-3-[1-(2-oxopiperidin-1-yl)pyridinium-4-thiomethyl]ceph-3-em-4-carboxylate halide Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.08 g, 0.1 mmol) was dissolved in dry dichloromethane (10 ml) and treated at room temperature with 1-(2-oxopiperidin-1-yl)-4-thiopyridone (0.0229 g, 0.11 mmol). After stirring the reaction mixture at room temperature for 3 h, the mixture was poured into rapidly stirred diethyl ether (100 ml). The resulting precipitate (0.079 g, 78%) was collected by filtration, washed with diethyl ether and dried under reduced pressure; $\nu_{max}$ (KBr) 1786, 1710sh, 1685 and 1616 cm$^{-1}$; $\delta_H$(CD$_3$OD) 1.21 (3H, t, J 7 Hz), 1.98–2.22 (4H, m), 2.66 (2H, t, J 7 Hz), 3.12 and 3.21 (2H, ABq, J 16 Hz), 3.37–3.69 (4H, m), 3.94 (2H, t, J 6 Hz), 3.99–4.10 (2H, m), 4.43 and 4.50 (2H, ABq, J 11 Hz), 5.45 (1H, s), 5.58 (1H, d, J 7 Hz), 6.98 (1H, s), 7.20–7.60 (15H, m), 7.91 (2H, d, J 7 Hz), 8.17 (1H, s), 8.64 (2H, d, J 7 Hz), and 9.98 (1H, d, J 7 Hz, exch.); m/z (positive xenon, F.A.B., thioglycerol) M+ 931.

b) [6R,7R]-7-[[R]-2-[(4-Ethyl-2,3-dioxopiperazin-1-yl)carbonylamino]-2-phenylacetamido]-7-formamido-3-[1-(2-oxopiperidin-1-yl)pyridinium-4-thiomethyl]ceph-3-em-4-carboxylate The product of Example 22(a) (0.079 g, 0.08 mmol) in dry dichloromethane (5 ml) was treated with trifluoroacetic acid (0.267 g, 2.3 mmol) at room temperature. After 1 h the volatiles were removed under reduced pressure and the residue treated with water (10 ml) and the pH adjusted to 8.0 by addition of saturated, aqueous sodium hydrogen carbonate solution. This mixture was chromatographed on HP20SS resin, eluting with mixtures of tetrahydrofuran in water, to give the title compound (0.032 g, 53%); $\nu_{max}$ (KBr) 1773, 1710sh, 1676 and 1616 cm$^{-1}$; $\delta_H$(D$_2$O) 1.15 (3H, t, J 7 Hz), 1.85–2.24 (4H, 2m), 2.65 (2H, t, J 6 Hz), 2.97 and 3.37 (2H, ABq, J 17 Hz), 3.47 (2H, q, J 7 Hz), 3.64 (2H, brm), 3.86–4.08 (4H, m), 4.14 and 4.23 (2H, ABq, J 14 Hz), 5.22 (1H, s), 5.46 (1H, s), 7.30–7.58 (5H, m), 7.93 (2H, d, J 6 Hz), 8.09 (1H, s), and 8.55 (2H, d, J 6 Hz); m/z (positive xenon F.A.B., thioglycerol) MH+ 765.

EXAMPLE 23

[6R,7R]-7-[[R]-2-[(4-Ethyl-2,3-dioxopiperazin-1-yl)carbonylamino]-2-phenylacetamido]-7-formamido-3-[1-[(prop-2-en-1-yl)amino]pyridinium-4-thiomethyl]ceph-3-em-4-carboxylate Diphenylmethyl [6R,7R]-7-[[R]-2-[(4-ethyl-2,3-dioxopiperazin-1-yl)carbonylamino]-2-phenylacetamido]-7-formamido-3-(halomethyl)ceph-3-em-4-carboxylate (0.128 g, 0.159 mmol) in acetone (5 ml) was treated with sodium iodide (0.024 g, 0.161 mmol). The mixture was stirred for 0.5 h, filtered and evaporated under reduced pressure. The product was then dissolved in dichloromethane (2 ml) and treated with 1-[N-(t-butyloxycarbonyl)-N-(prop-2-en-1-yl)amino]-4-thiopyridone (0.045 g, 0.169 mmol) in dichloromethane (2 ml). The reaction mixture was stirred for 4.5 h, and then evaporated under reduced pressure. The crude product was dissolved in trifluoroacetic acid (2 ml) and the reaction mixture was stirred for 10 minutes, toluene (10 ml) was added and evaporated under reduced pressure. Purification on Diaion HP20SS resin gave the title compound (0.041 g, 36%); $\nu_{max}$(KBr) 1776, 1677, and 1618 cm$^{-1}$; $\delta_H$(D$_2$O) 1.15 (3H, d, J 7 Hz), 2.93 and 3.33 (2H, ABq, J 17 Hz), 3.48 (2H, q, J 7 Hz)), 3.60–3.71 (2H, m), 3.85 (2H, d, J 7 Hz), 3.88–4.00 (2H, m), 4.03 and 4.33 (2H, ABq, J 14 Hz), 5.05–5.25 (2H, m), 5.19 (1H, s), 5.46 (1H, s), 5.79–5.95 (1H, m), 7.33–7.54 (5H, m), 7.75 (2H, d, J 7 Hz), 8.09 (1H, s), and 8.43 (2H, d, J 7 Hz); m/z (positive xenon F.A.B., thioglycerol) MH+ 723.

EXAMPLE 24

[6R,7R]-7-[[R]-2-(3,4-Dihydroxyphenyl)-2-[(4-ethyl-2,3-dioxopiperazin-1-yl)carbonylamino]acetamido]-7-formamido-3-1-(methylamino)pyridinium-4-thiomethyl]ceph-3-em-4-carboxylate a) Diphenylmethyl [6R,7R1-7-[[R]-2-(3,4-diacetoxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate iodide Diphenylmethyl [6R,7R]-7-[[R]-2-[(3,4-diacetoxyphenyl)-2-(4-ethyl-2,3-dioxopiperazin-1-yl)carbonylamino]acetamido]-7-formamido-3-(halomethyl)-ceph-3-em-4-carboxylate (0.1 g, 0.114 mmol) in dichloromethane (2 ml) was treated with 1-(methylamino)-4-thiopyridone (0.016 g, 0.114 mmol) and sodium iodide (0.016 g, 0.114 mmol). The mixture was stirred for 3 h and then filtered and evaporated under reduced presure. Purification on silica gel 60 eluting with ethanol, dichloromethane mixtures gave the title compound (0.078 g, 70%); $\nu_{max}$ (KBr) 1993, 1777, 1680, and 1619 cm$^{-1}$; $\delta_H$ (CDCl$_3$) 1.27 (3H, t, J 7 Hz), 2.27 (6H, 2s), 2.81 (2H, ABq, J 17 Hz), 2.93 (3H, s), 3.34–3.80 (4H, m), 3.90–4.20 (2H, m), 4.70–4.87 (2H, m), 5.52 (1H, s), 6.05 (1H, m), 6.93 (1H, s), 7.10–7.68 (13H, m), 7.72 (2H, d, J 7 Hz), 8.24 (1H, s), and 8.42 (2H, d, J 7 Hz); m/z (positive xenon F.A.B., thioglycerol) M+ 979.

b) [6R,7R1-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate The product from Example 24(a) (0.078 g, 0.08 mmol) was treated with trifluoroacetic acid (2 ml) and stirred for 10 minutes, toluene (2 ml) was added and the mixture filtered through celite on to vigorously stirred diethyl ether. The resulting precipitate was filtered off and dissolved in methanol (2 ml). Water (2 ml) was then added and the solution adjusted to pH 8.5 using dilute aqueous sodium hydroxide solution. The solution was maintained at pH 8.5 for 1 h, then acidified to pH 7.0 using dilute acetic acid and the organic solvent removed by evaporation under reduced pressure. Purification on Diaion HP20SS resin eluting with mixtures of water and acetone gave the title compound (0.011 g, 19%); $\nu_{max}$ (KBr) 1771, 1678, 1617 and 1512 cm$^{-1}$; $\delta_H$ (D$_2$O) 1.13 (3H, t, J 7 Hz), 2.99 (3H, s), 2.94 and 3.33 (2H, ABq, J 17 Hz), 3.47 (2H, ABq, J 7 Hz), 3.57–3.77 (2H, m), 3.90–4.20 (2H, m), 4.08 and 4.29 (2H, ABq, J 12 Hz), 5.21 (1H, s), 5.29 (1H, s), 6.76–7.00 (3H, m), 7.77 (2H, d, J 7 Hz), 8.08 (1H, s), and 8.49 (2H, d, J 7 Hz); m/z (positive xenon F.A.B., thioglycerol) MH+ 729.

EXAMPLE 25

[6R,7R]-3-(1-Aminopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4carboxylate a) Diphenylmethyl [6R,7R]-3-(1-Aminopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate iodide Diphenylmethyl [6R,7R]-7-[[R]-2-(3,4-dihydroxyphenyl)-2-[(4-ethyl-2,3-dioxopiperazin-1-yl)carbonylamino]acetamido]-7-formamido-3-(halomethyl)-ceph-3-em-4-carboxylate (0.9 g, 1.1 mmol) in acetonitrile (50 ml) was treated successively with sodium iodide (0.16 g, 1.1 mmol) and a solution of 1-amino-4-thiopyridone (0.17 g, 1.3 mmol) in N,N-dimethylformamide (3 ml). The reaction mixture was stirred for 3 h, then concentrated to a small volume (ca. 5 ml) before being added to vigorously stirred diethyl ether (50 ml). The precipitate was filtered and dried to give a quantitative recovery of the title compound; $\delta_H$ (CDCl$_3$+CD$_3$OD) 1.23 (3H, t, J 7 Hz), 2.99 and 3.12 (2H, ABq, J 16 Hz), 3.56 (2H, q, J 7 Hz), 3.62 (2H, m), 4.05 (2H, m), 4.40 (MeOD covering 2H), 5.26 (1H, d, J 6 Hz), 5.35 (1H, s), 6.70–6.97 (4H, m), 7.15–7.59 (10H, m), 7.65 (2H, d, J 7 Hz), 7.98 (1H, s), 8.39 (2H, d, J 7 Hz), and 9.75 (1H, d, J 6 Hz); m/z (F.A.B., thioglycerol) M+ 881.

b) [6R,7R]-3-(1-Aminopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate The product of Example 25(a) (1.1 g, 1.1 mmol) was treated with trifluoroacetic acid (5 ml) and stirred for 5 minutes. The mixture was diluted with a little toluene, filtered through celite, and added to diethyl ether (50 ml). The precipitate was filtered off and dried. The solid obtained was partially dissolved in acetonitrile and water and the mixture adjusted to pH 7.0 with sodium hydrogen carbonate solution. The organic solvent was removed under reduced pressure and the aqueous mixture purified on Diaion HP20SS resin eluting with tetrahydrofuran, water mixtures to give the title compound (0.21 g, 27%); $\nu_{max}$ (KBr) 1773, 1709, 1675, and 1610 cm$^{-1}$; $\delta_H$(D$_2$O) 1.20 (3H, t, J 7 Hz), 3.09 and 3.34 (2H, ABq, J 17 Hz), 3.52 (2H, q, J 7 Hz), 3.72 (2H, m), 4.03 (2H, m), 4.17 and 4.34 (2H, ABq, J 14 Hz), 5.26 (1H, s), 5.36 (1H, s), 6.74–6.98 (3H, m), 7.85 (2H, d, J 6 Hz), 8.14 (1H, s), and 8.46 (2H, m); m/z (positive xenon F.A.B., thioglycerol) MH+ 715, MNa+ 737.

EXAMPLE 26

[6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate a) Diphenylmethyl [6R,7R]-7-[[R]-2-(3,4-dihydroxyphenyl)-2-[(4-ethyl-2,3-dioxopiperazin-1-yl)carbonylamino]acetamido]-7-formamido-3-[1-(methylamino)pyridinium-4-thiomethyl]-ceph-3-em-4-carboxylate iodide Diphenylmethyl [6R,7R]-7-[[R]-2-(3,4-dihydroxyphenyl)-2-[(4-ethyl-2,3-dioxopiperazin-1-yl)carbonylamino]-7-formamido-3-(halomethyl)ceph-3-em-4-carboxylate (0.65 g, 0.82 mmol) in acetonitrile (30 ml) was treated successively with 1-(methylamino)-4-thiopyridone (0.144 g, 0.99 mmol) and sodium iodide (0.123 g, 0.82 mmol). The reaction mixture was stirred for 1.5 h, then filtered through celite and evaporated to low volume (5 ml) under reduced pressure. The solution was added to diethyl ether and the precipitate filtered and dried to give the title compound (0.309 g, 37%); $\nu_{max}$ (CH$_2$Cl$_2$) 1782, 1710, 1676, and 1617 cm$^{-1}$; $\delta_H$(CDCl$_3$+CD$_3$OD) 1.23 (3H, t, J 7 Hz), 2.76 and 3.01 (2H, ABq, J 16 Hz), 3.05 (3H, s), 3.40–3.70 (4H, m), 4.04 (4H, m), 5.31 (1H, s), 5.35 (1H, s), 6.75–7.00 (3H, m), 7.20–7.59 (10H, m), 7.70 (2H, d, J 7 Hz), 8.21 (1H, s), and 8.50 (2H, d, J 7 Hz); m/z (positive xenon F.A.B., 3-nitrobenzylalcohol, sodium acetate) M+ 895.

b) [6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate The product of Example 26(a) (0.30 g, 0.29 mmol) was treated with trifluoroacetic acid (2 ml) and stirred for 5 minutes. The mixture was filtered through celite, washing the solids with a little toluene. The filtrate was added to diethyl ether and the precipitate filtered and dried. The crude product was dissolved in acetonitrile and water. The organic solvent was evaporated under reduced pressure and the aqueous mixture purified on Diaion HP20SS resin eluting with tetrahydrofuran, water mixtures to give the title compound (0.088 g, 41%), which was identical to the product of Example 24(b).

EXAMPLE 27

Sodium [6R,7R]-3-[1-(Carboxymethylamino)pyridinium-4-thiomethyl]-7-[[R]-2-(3,4-dihydroxyphenyl)-2-[(4-ethyl-2,3-dioxopiperazin-1-yl)carbonylamino]acetamido]-7-formamidoceph-3-em-4-carboxylate a) Diphenylmethyl [6R,7R]-3-[1-[N-(t-butyloxycarbonyl)-N-(t-butyloxycarbonylmethyl)amino]pyridinium-4-thiomethyl]-7-[[R]-2-(3,4-dihydroxyphenyl)-2-[(4-ethyl-2,3-dioxopiperazin-1-yl)carbonylamino]acetamido]-7-formamidoceph-3-em-4-carboxylate iodide Diphenylmethyl [6R,7R]-7-[[R]-2-(3,4-dihydroxyphenyl)-2-[(4-ethyl-2,3-dioxopiperazin-1-yl)carbonylamino]acetamido]-7-formamido-3-(halomethyl)-ceph-3-em-4-carboxylate (0.30 g, 0.38 mmol) in acetonitrile (5 ml) with sodium iodide (0.057 g, 0.38 mmol) was treated with 1-[N-(t-butyloxycarbonyl)-N-(t-butyloxycarbonylmethyl)amino]-4-thiopyridone (0.14 g, 0.41 mmol). The mixture was stirred for 3 h, then filtered through celite. The filtrate was added to vigorously stirred diethyl ether (50 ml). The precipitate was filtered off and dried to give the title compound (0.323 g, 71%); $\nu_{max}$(KBr) 1786, 1717, 1683, and 1616 cm$^{-1}$; $\delta_H$ (CDCl$_3$+CD$_3$OD) 1.24 (3H, t, J 7 Hz), 1.53 (18H, s), 2.80–3.10 (2H, m), 3.56 (2H, q, J 7 Hz), 3.64 (2H, m), 4.07 (2H, m), 4.44 (1H, d, J 14.5 Hz), 4.62 (2H, s), 4.68 (MeOD covering 1H), 5.37 (1H, d, J 6 Hz), 5.37 (1H, s), 6.72–6.99 (4H, m), 7.20–7.60 (10H, m), 7.82 (2H, d, J 7 Hz), 8.21 (1H, s), 8.65 (2H, d), and 9.78 (1H, d, J 6 Hz); m/z (F.A.B., thioglycerol) M+ 1095.

b) Sodium [6R,7R]-3-[1-(carboxymethylamino)pyridinium-4-thiomethyl-7-[[R]-2-(3,4-dihydroxyphenyl)-2-[(4-ethyl-2,3-dioxopiperazin-1-yl)carbonylamino]acetamido]-7-formamidoceph-3-em-4-carboxylate A product of Example 27(a) (0.30 g, 0.25 mmol) was treated with trifluoroacetic acid (2 ml) and stirred for 5 minutes. The mixture was filtered through celite and the filtrate added to diethyl ether (30 ml). The mixture was diluted with toluene (5 ml) and evaporated to dryness under reduced pressure. The residue was suspended in water (15 ml) and neutralised with aqueous sodium hydrogen carbonate to pH 7.0. Purification on Diaion HP20SS resin eluting with tetrahydrofuran and water mixtures gave the title compound (0.089 g, 45%); $\nu_{max}$ (KBr) 1771, 1710, 1675, and 1611 cm$^{-1}$; $\delta_H$(D$_2$O) 1.15 (3H, t, J 7 Hz), 2.95 and 3.35 (2H, ABq, J 17 Hz), 3.47 (2H, q, J 7 Hz), 3.66 (2H, m), 3.90 (2H, s), 3.97 (2H, m), 4.12 and 4.25 (2H, ABq, J 14 Hz), 5.23 (1H, s), 5.30 (1H, s), 6.76–7.01 (3H, m), 7.75 (2H, d, J 7 Hz), 8.09 (1H, s), and 8.54 (2H, d, J 7 Hz); m/z (F.A.B., thioglycerol) MH+ 795, MNa+ 817.

EXAMPLE 28

[6R,7R]-3-(1-Amino-2,3-cyclopentenopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate a) Diphenylmethyl [6R,7R]-3-1-(t-butoxycarbonylamino)-2,3-cyclopentenopyridinium-4-thiomethyl]-7-[[R]-2-(3,4-dihydroxyphenyl)-2-[(4-ethyl-2,3-dioxopiperazin-1-yl)carbonylamino]acetamido]-7-formamidoceph-3-em-4-carboxylate Diphenylmethyl [6R,7R]-7-[[R]-2-(3,4-dihydroxyphenyl)-2-[(4-ethyl-2,3-dioxopiperazin-1-yl)carbonylamino]acetamido]-7-formamido-3-(halomethyl)-ceph-3-em-4-carboxylate (0.5 g, 0.68 mmol) in dichloromethane (5 ml) was treated with 1-(t-butyloxycarbonylamino)-2,3-cyclopenteno-4-thiopyridone (0.2 g, 0.75 mmol) and sodium iodide (0.94 g, 0.63 mmol). The mixture was stirred at room temperature for 4 h, then filtered and evaporated under reduced pressure to dryness. Purification on silica gel 60 eluting with ethanol, dichloromethane (1:9) gave the title compound (0.284 g, 46%); $\delta_H$ (CDCl$_3$); (interalia) 1.17–1.3 (3H, m), 1.56 (9H, s), 2.28–2.47 (2H, m), 2.89 (1H, d), 2.95–3.13 (2H, m), 3.25–3.45 (3H, m), 3.5–3.71 (4H, m), 4.05 (2H, d, J 7.9 Hz), 4.6–4.81 (2H, m), 5.28 (1H, s), 5.37 (1H, s), 6.75–7.0 (4H, m), 7.2–7.58 (10H, m), 7.64 (1H, d, J 6.9 Hz), 8.0 (1H, d, J 6.9 Hz), and 8.22 (1H, s); m/z (F.A.B., thioglycerol) MH+ 1022.

b) [6R,7R]-3-(1-Amino-2,3-cyclopentenopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate The product of Example 28(a) (0.28 g, 0.28 mmol) was treated with trifluoroacetic acid and the mixture was stirred for 3 min at room temperature, toluene (10 ml) was added and the mixture was evaporated under reduced pressure to dryness. Purification on Diaion HP20SS resin gave the title compound (0.05 g, 24%); $\nu_{max}$(KBr) 1782, 1675, and 1512 cm$^{-1}$; $\delta_H$(D$_2$O+CD$_3$OD) 0.93 (3H, t, J 7.1 Hz), 2.17–2.34 (2H, m), 2.81–3.9 (2H, ABq, J 16.4 Hz), 2 92 (2H, t, J 7.3 Hz), ca. 3.2 (2H, m, obscured by CD$_3$OH), 3.43 (2H, q, J 7.1 Hz), 3.55–3.68 (2H, m), 3.92 (2H, d), 4.22 and 4.35 (2H, ABq, J 14.2 Hz), 5.17 (1H, s), 5.25 (1H, d, partially exchanged), 6.7–6.93 (3H, m), 7.52 (1H, d, J 6.9 Hz), 8.05 (1H, s), 8.18 (1H, d, J 6.8 Hz), and 9.73 (1H, d, partially exchanged, J 5.7 Hz); m/z (F.A.B., thioglycerol) MH+ 755.

EXAMPLE 29

[6R,7R]-3-(1-Aminopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate hydrochloride

[6R,7R]-3-(1-Aminopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate (0.10 g, 0.14 mmol) was stirred with 2M HCl (0.5 ml) and tetrahydrofuran (0.5 ml). After 2 minutes the organic solvent was removed under reduced pressure and the solution was added to propan-2-ol (10 ml). The precipitate was filtered and dried to give the title compound (0.056 g, 53%); $\delta_H$ (D$_2$O) 1.15 (3H, t, J 7 Hz), 2.82 and 3.23 (2H, ABq, J 16.5 Hz), 3.47 (2H, q, J 7 Hz), 3.65 (2H, m), 3.92–4.04 (2H, m), 4.22 and 4.33 (2H, ABq, J 14.5 Hz), 5.24 (1H, s), 5.30 (1H, s), 6.81–6.99 (3H, m), 7.73 (2H, d, J 7 Hz), 8.10 (1H, s), and 8.38 (2H, d, J 7 Hz).

We claim:

1. A compound of formula (I) or a pharmaceutically acceptable salt thereof:

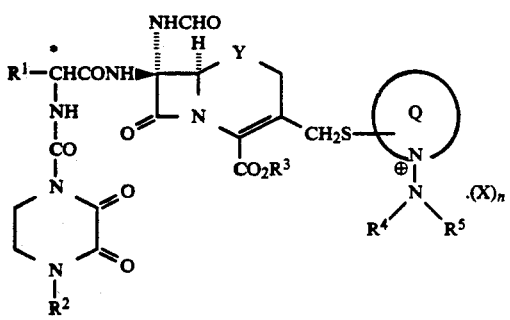

in which:

Y is sulphur, —SO—, or —SO$_2$—;

$R^1$ is phenyl, phenyl substituted with up to five substituents selected from the group consisting of halogen, (C$_{1-6}$)alkyl, phenyl, (C$_{1-6}$)alkoxy, hydroxy-(C$_{1-6}$)alkyl, mercapto(C$_{1-6}$)alkyl, halo(C$_{1-6}$)alkyl, mercapto, hydroxy, amino, mono- or di-(C$_{1-6}$)alkylamino, nitro, carboxy, (C$_{1-6}$)alkoxycarbonyl, (C$_{1-6}$)alkoxycarbonyl(C$_{1-6}$)alkyl, (C$_{1-6}$)alkylcarbonyloxy, formyl, and (C$_{1-6}$)alkylcarbonyl, cyclohexenyl, cyclohexadienyl, 1-hydroxyethyl, 2-methylthioethyl or a 5- or 6- membered heterocyclic ring containing up to three heteroatoms selected from the group consisting of oxygen, sulphur and nitrogen, and further which is unsubstituted or substituted with hydroxy, amino, halogen, (C$_{1-6}$)alkylamino, di(C$_{1-6}$alkyl) amino or (C$_{1-6}$)alkoxy;

$R^2$ is (C$_{1-6}$)alkyl;

CO$_2$R$^3$ is carboxy or a carboxylate anion, or the group R$^3$ is a readily removable carboxy protecting group;

the moiety:

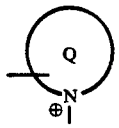

(the ring Q) is a pyridinium group bonded to sulphur by a ring carbon atom and which is unsubstituted or substituted at a ring carbon atom available for substitution by up to four substituents, two of which may be linked to form the residue of a 4, 5, 6 or 7-membered heterocyclic ring which is aromatic or non-aromatic, single or fused, containing up to four heteroatoms selected from the group consisting of oxygen, nitrogen and sulphur, or a carboxycyclic ring;

$R^4$ and $R^5$ which may be the same or different are hydrogen, substituted or unsubstituted (C$_{1-6}$)alkyl, substituted or unsubstituted (C$_{3-7}$)cycloalkyl, substituted or unsubstituted (C$_{5-8}$)cycloalkenyl, substituted or unsubstituted (C$_{2-6}$)alkenyl, substituted or unsubstituted (C$_{2-6}$)alkynyl, substituted or unsubstituted (C$_{1-6}$)alkylcarbonyl, substituted or unsubstituted (C$_{1-6}$)alkoxycarbonyl, substituted or unsubstituted (C$_{2-6}$)alkenylcarbonyl, substituted or unsubstituted mono- and di-(C$_{1-6}$alkyl) carbamoyl, substituted or unsubstituted (C$_{1-6}$)alkylsulphonyl, substituted unsubstituted hydrazinocarbonyl(C$_{1-6}$)alkyl, phenyl, naphthyl, a 4, 5, 6 or 7-membered aromatic or non-aromatic, single or fused heterocyclic ring structure containing up to four heteroatoms selected from the group consisting of oxygen, nitrogen and sulphur, phenylcarbonyl, naphthylcarbonyl, heterocyclylcarbonyl wherein said heterocyclyl moiety is a 4, 5, 6 or 7-membered aromatic or non-aromatic, single or fused, heterocyclic ring structure containing up to four heteroatoms selected from the group consisting of oxygen, nitrogen and sulphur, carbamoyl, mono- and di-phenylcarbamoyl, mono- and di-naphthylcarbamoyl, N-(substituted or unsubstituted (C$_{1-6}$)alkyl)N-phenyl- or N-naphthyl-carbamoyl, phenylsulphonyl, naphthylsulphonyl, formyl, sulphonyl, N-acylcarbamoyl, or a readily removable amino protecting group, substituted (C$_{1-6}$)alkyl, substituted (C$_{3-7}$)cycloalkyl, substituted (C$_{5-8}$)cycloalkenyl, substituted (C$_{2-6}$)alkenyl, substituted (C$_{2-6}$)alkynyl, substituted (C$_{1-6}$)alkylcarbonyl, substituted (C$_{1-6}$)alkoxycarbonyl, substituted (C$_{2-6}$)alkenylcarbonyl, substituted mono- and di-(C$_{1-6}$ alkyl)carbamoyl, substituted (C$_{1-6}$)alkylsulphonyl, substituted hydrazinocarbonyl(C$_{1-6}$) alkyl or N-(substituted(C$_{1-6}$)alkyl)N-phenyl- or N-naphthylcarbamoyl wherein a substituent for alkyl, cycloalkyl, alkenyl, cycloalkenyl, or alkynyl is selected from the group consisting of halogen, cyano, azido, nitro, carboxy, (C$_{1-6}$)alkoxycarbonyl, carbamoyl, mono- or di-(C$_{1-6}$)alkylcarbamoyl, sulphono, sulphamoyl, mono- and di-(C$_{1-6}$)alkylsulphamoyl, amino, mono- and di-(C$_{1-6}$)alkylamino, acylamino, (C$_{1-6}$)alkoxycarbonylamino, naphthyl, phenyl, heterocyclyl, hydroxy, (C$_{1-6}$)alkoxy, acyloxy, oxo, phenylcarbonyl, naphthylcarbonyl, heterocyclylcarbonyl (C$_{1-6}$)alkylthio, (C$_{1-6}$)alkanesulphinyl, and (C$_{1-6}$)alkanesulphonyl; or $R^4$ and $R^5$ together with the nitrogen atom to which they are attached form an amidine or a 4, 5, 6 or 7-membered heterocyclic ring which is aromatic or non-aromatic, single or fused, containing up to four heteroatoms selected from the group consisting of oxygen, nitrogen and sulphur or; $R^4$ and $R^5$ together form a (C$_{1-6}$)alkylidene, (C$_{1-7}$)-cycloalkylidene, phenyl (C$_{1-6}$)alkylidene, naphthyl-(C$_{1-6}$)alkylidene or heterophenyl(C$_{1-6}$)alkylidene or heteronaphthyl-(C$_{1-6}$)alkylidene wherein the heteroatoms are selected from the group consisting of oxygen, nitrogen and sulphur, and which alkylidene or cycloalkylidene moiety is unsubstituted or substituted with a substituent selected from the group consisting of halogen, cyano, azido, nitro, carboxy, (C$_{1-6}$)alkoxycarbonyl, carbamoyl, mono- or di-(C$_{1-6}$)alkylcarbamoyl, sulphono, sulphamoyl, mono- and di-(C$_{1-6}$)alkylsulphamoyl, amino, mono- and di-(C$_{1-6}$)alkylamino, acylamino, (C$_{1-6}$)alkoxycarbonylamino, naphthyl, phenyl, a 4, 5, 6 or 7-membered aromatic or non-aromatic, single or fused, heterocyclic ring structure containing up to four heteroatoms selected from the group consisting of oxygen, nitrogen and sulphur, hydroxy, (C₁₋₆)alkoxy, acyloxy, oxo, phenylcarbonyl, naphtylcarbonyl, heterocyclylcarbonyl, (C₁₋₆)alkylthio, (C₁₋₆)alkanesulphinyl, and (C₁₋₆) alkanesulphonyl; X is an inorganic or organic anion; n is 0 or 1, with the proviso that when:

(i) $CO_2R^3$ is carboxylate, n is 0, and (ii) $CO_2R^3$ is carboxy or the group $R^3$ is readily removable carboxy protecting group, then n is 1 and the anion X is present in the appropriate stoichiometric proportion to balance the positive charge on the pyridinium group; and

* denotes an asymmetric carbon atom.

2. A compound of formula (Ia) or pharmaceutically acceptable salt or a pharmaceutically acceptable in vivo hydrolysable ester thereof:

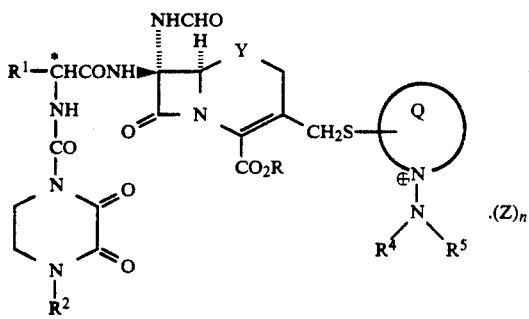
(Ia)

in which $R^1$, $R^2$, $R^4$, $R^5$, ring Q, Y, n, and * are as defined with respect to formula (I) with the proviso that neither $R^4$ or $R^5$ is a readily removable amino protecting group, the group $CO_2R$ is carboxy or a carboxylate anion and Z is a pharmaceutically acceptable inorganic or organic anion present in the appropriate stoichiometric proportion to balance the positive charge on the ring Q.

3. A compound of the formula (Ib):

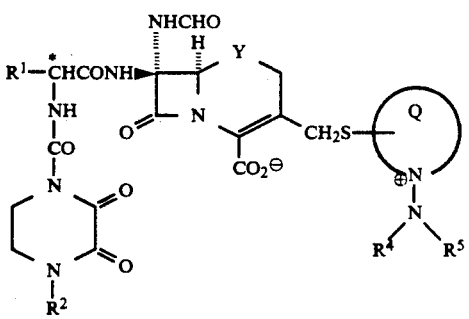
(Ib)

wherein $R^1$, $R^2$, $R^4$, $R^5$, Y, ring Q and * are defined with respect to formula (Ia).

4. A compound of the formula (Ic):

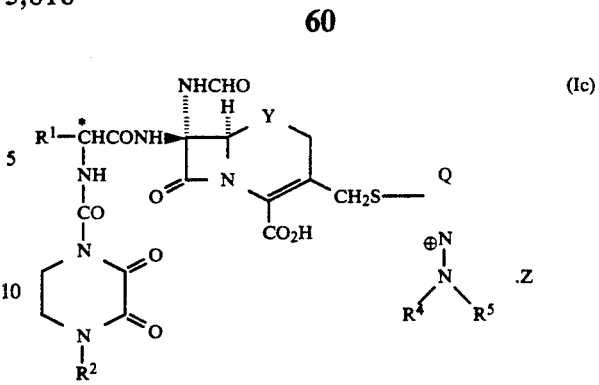
(Ic)

wherein $R^1$, $R^2$, $R^4$, $R^5$, Y, Z, ring Q and * are defined with respect to formula (Ia).

5. A compound as claimed in claim 1 in which $R^1$ is a phenyl group substituted with up to three groups selected from (C₁₋₆)alkyl, phenyl, halogen, amino, nitro, hydroxy, (C₁₋₆)alkylamido, carbamoyl, carboxy, (C₁₋₆)alkoxycarbonyl, aryloxycarbonyl, halo(C₁₋₆)alkyl, hydroxy(C₁₋₆)alkyl, oxo(C₁₋₆)alkyl, (C₁₋₆)alkylcarbonyl, arylcarbonyl, (C₁₋₆)alkylamino, di(C₁₋₆)alkylamino, or sulphonamido, any amino and hydroxy groups being unprotected or protected.

6. A compound as claimed in claim 5 in which $R^1$ is selected from the group consisting of 3,4-dihydroxyphenyl, 3,4-diacetoxyphenyl, 4-hydroxyphenyl, 4-acetoxyphenyl, 4-aminophenyl, 2-thienyl and 1-hydroxyethyl.

7. A compound as claimed in claim 1 in which is $R^2$ is (C₁₋₆)alkyl.

8. A compound as claimed in claim 7 in which $R^2$ is ethyl.

9. A compound as claimed in claim 1 in which $R^4$ and $R^5$ are each selected from the group consisting of unsubstituted (C₁₋₆)alkyl, unsubstituted (C₂₋₆)alkenyl, hydrogen, naphthyl or phenyl, unsubstituted (C₀₋₆)alkylcarbonyl, phenylcarbonyl, naphthylcarbonyl, heterocyclylcarbonyl wherein the heterocyclyl moiety is a 4, 5, 6 or 7-membered aromatic or non-aromatic, single or fused, heterocyclic ring structure containing up to four heteroatoms selected from the group consisting of oxygen, nitrogen and sulphur, substituted (C₁₋₆)alkyl, substituted (C₂₋₆)alkenyl and substituted (C₀₋₆)alkylcarbonyl, wherein a substituent for alkyl or alkenyl is selected from the group consisting of halogen, cyano, azido, nitro, carboxy, (C₁₋₆)alkoxycarbonyl, carbamoyl, mono- or di-(C₁₋₆)alkylcarbamoyl, sulphono, sulphamoyl, mono- and di-(C₁₋₆)alkylsulphamoyl, amino, mono- and di-(C₁₋₆)alkylamino, acylamino, (C₁₋₆)alkoxycarbonylamino, naphthyl, phenyl, a 4, 5, 6 or 7-membered aromatic or non-aromatic, single or fused heterocyclic ring structure containing up to four heteroatoms selected from the group consisting of oxygen, nitrogen and sulphur, hydroxy, (C₁₋₆)alkoxy, acyloxy, oxo, phenylcarbonyl, naphthylcarbonyl, heterocyclylcarbonyl, (C₁₋₆)alkylthio, (C₁₋₆)alkanesulphinyl, and (C₁₋₆)alkanesulphonyl, or the groups $R^4$ and $R^5$ together with the nitrogen atom to which they are attached form a 4, 5, 6 or 7-membered heterocyclic ring which is aromatic or non-aromatic, single or fused, containing up to four heteroatoms selected from the group consisting of oxygen, nitrogen and sulphur.

10. A compound as claimed in claim 9 in which $R^4$ and $R^5$ are independently selected from the group consisting of hydrogen, methyl, ethyl, prop-2-en-1-yl, benzyl, phenyl, carbamoylmethyl, carboxymethyl, 2-hydroxyethyl, t-butoxycarbonylmethyl, formyl, acetyl, 3,4-dihydroxbenzoyl, p-nitrobenzoyl, p-methoxybenzoyl, 3,4-dihydroxycinnamoyl, and 2-furoyl; or the groups $R^4$ and $R^5$ and the nitrogen atom to which they are attached form a pyrrolidinyl, morpholinyl, piperazinyl, or a hexahydroazepinyl group.

11. A compound as claimed in claim 1 in which $R^5$ is hydrogen or $(C_{1-6})$alkyl.

12. A compound as claimed in claim 1 in which, in the ring Q, the pyridinium group is bonded to sulphur by a carbon α- or γ- to the pyridinium nitrogen.

13. A compound as claimed in claim 1 of the formula (II):

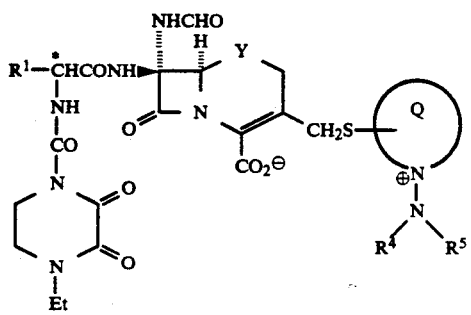

wherein $R^1$ is phenyl or substituted phenyl, and Y, $R^4$, $R^5$, ring Q, and * are as defined with respect to formula (I).

14. A compound as claimed in claim 1 selected from the group consisting of the following or a pharmaceutically acceptable salt and an in-vivo hydrolysable ester thereof:

[6R,7R]-3-[1-(3,4-Dihydroxybenzoylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(Dimethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(pyrrolidin-1-yl)pyridinium-4-thiomethyl]ceph-3-em-4-carboxylate;

[6R,7R]-3-[1-(N-Benzyl-N-methylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(N-Carbamoylmethyl-N-methylamino)-pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-(3,4-dihydroxybenzoyl)-N-methylamino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-(3,4-dihydroxycinnamoyl)-N-methylamino]-pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-methylamino)pyridinium-4-thiomethyl]ceph-3-em-4carboxylate;

[6R, 7R]-7-[[R]-2-[(4-Ethyl-2,3-dioxopiperazin-1-yl)carbonylamino]-2-phenylacetamido]-7-formamido-3-[1-(N-acetyl-N-methylamino)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(N-formyl-N-methylamino)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(4-nitrobenzoyl)amino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(4-methoxybenzoyl)amino]pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[N-methyl-N-(2-furoyl)amino]pyridinium-4-thiomethyl]ceph-3-em-4-carboxylate;

[6R,7R]-3-(1-Aminopyridinium-4-thiomethyl)-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(Carboxymethylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-3-[1-(Diphenylamino)pyridinium-4-thiomethyl]-7-[[R]-2-[(4-ethyl-2,3-dioxopiperazin-1-yl)carbonylamino]-2-phenylacetamido]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-[N-(2-hydroxyethyl)-N-methylamino]pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-(hexahydro-1H-azepin-1-yl)pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-[4-(2-hydroxyethyl)piperazin-1-yl]pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-3-[1-(morpholin-4-yl)pyridinium-4-thiomethyl]-7-formamidoceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(2-oxopyrrolidin-1-yl)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-(2-oxopiperidin-1-yl)pyridinium-4-thiomethyl]ceph-3-em-4-carboxylate;

[6R,7R]-7-[[R]-2-[(4-Ethyl-2,3-dioxopiperazin-1-yl)carbonylamino]-2-phenylacetamido]-7-formamido-3-[1-[(prop-2-en-1-yl)amino]pyridinium-4-thiomethyl]-ceph-3-em-4-carboxylate;

[6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4thiomethyl]ceph-3-em-4-carboxylate;

[6R,7R]-3-(1-Aminopyridinium-4-thiomethyl)-7-[[R]-2-(3,4-dihydroxyphenyl)-2-[(4-ethyl-2,3-dioxopiperazinlyl)carbonylamino]acetamido]-7-formamidoceph-3-em-4-carboxylate;

[6R,7R]-7-[[R]-2-(3,4-Dihydroxyphenyl)-2-[(4-ethyl-2,3-dioxopiperazin-1-yl)carbonylamino]acetamido]-7-formamido-3-[1-(methylamino)pyridinium-4-thiomethyl]ceph-3-em-4-carboxylate;

[6R,7R]-3-[1-(Carboxymethylamino)pyridinium-4-thiomethyl]-7-[[R]-2-(3,4-dihydroxyphenyl)-2-[(4-ethyl-2,3-dioxopiperazin-1-yl)carbonylamino]acetamido]-7-formamidoceph-3-em-4-carboxylate; and

[6R,7R]-3-(1-Amino-2,3-cyclopentenopyridinium-4-thiomethyl)-7-[[R]-2-(3,4-dihydroxyphenyl)-2-[(4-ethyl-2,3-dioxopiperazin-1-yl)carbonylamino]acetamido]-7-formamidoceph-3-em-4-carboxylate.

15. A method of treating bacterial infection which method comprises administering a therapeutically effective amount of a pharmaceutically acceptable compound as claimed in claim 1 to a patient in need thereof.

16. A method according to claim 15, wherein said compound is the compound according to claim 2.

17. A pharmaceutical composition comprising a pharmaceutically acceptable compound of formula (Ia) as claimed in claim 2 together with a pharmaceutically acceptable excipient or carrier.

18. A composition as claimed in claim 17 which further comprises a β-lactamase inhibitor.

* * * * *